US009804181B2

(12) United States Patent
German et al.

(10) Patent No.: US 9,804,181 B2
(45) Date of Patent: Oct. 31, 2017

(54) AUTOMATION TUBE POSITIONING METHODOLOGY

(71) Applicant: Siemens Healthcare Diagnostics Inc., Tarrytown, NY (US)

(72) Inventors: Ryan German, Riverdale, NJ (US); Benjamin S. Pollack, Budd Lake, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 197 days.

(21) Appl. No.: 14/760,689

(22) PCT Filed: Jan. 14, 2014

(86) PCT No.: PCT/US2014/011523
§ 371 (c)(1),
(2) Date: Jul. 13, 2015

(87) PCT Pub. No.: WO2014/113401
PCT Pub. Date: Jul. 24, 2014

(65) Prior Publication Data
US 2015/0355208 A1 Dec. 10, 2015

Related U.S. Application Data

(60) Provisional application No. 61/752,861, filed on Jan. 15, 2013.

(51) Int. Cl.
*G01N 35/00* (2006.01)
*G01N 35/02* (2006.01)
(Continued)

(52) U.S. Cl.
CPC .......... *G01N 35/021* (2013.01); *B65G 43/08* (2013.01); *G01N 35/0095* (2013.01);
(Continued)

(58) Field of Classification Search
CPC ......... B65G 43/08; G01N 2035/00326; G01N 2035/00881; G01N 2035/0406;
(Continued)

(56) References Cited

U.S. PATENT DOCUMENTS 3,883,306 A * 5/1975 Widen ................. G01N 35/026
422/64
4,113,436 A * 9/1978 Werder ................ G01N 35/021
422/65
(Continued)

FOREIGN PATENT DOCUMENTS

EP 1 028 320 B1 3/2006

OTHER PUBLICATIONS

PCT International Search Report and Written Opinion dated Apr. 22, 2014 (13 Pages).

*Primary Examiner* — Maureen Wallenhorst

(57) ABSTRACT

Methods and systems allow characterization of sample vessels and carriers in an automation system to determine any physical deviation from nominal positions. In response, an offset can be calculated and applied when positioning a carrier relative to a station, such as a testing or processing stations (or vice-versa). This may allow for precise operation of an instrument with a sample vessel on an automation track, while compensating for deviation in manufacturing and other tolerances.

34 Claims, 18 Drawing Sheets

(51) Int. Cl.
*G01N 35/04* (2006.01)
*G01N 35/10* (2006.01)
*B65G 43/08* (2006.01)

(52) U.S. Cl.
CPC ... *G01N 35/0099* (2013.01); *G01N 35/00871* (2013.01); *G01N 35/04* (2013.01); *G01N 35/1011* (2013.01); *G01N 2035/00326* (2013.01); *G01N 2035/00881* (2013.01); *G01N 2035/0406* (2013.01); *G01N 2035/0462* (2013.01); *G01N 2035/0494* (2013.01); *Y10T 436/113332* (2015.01)

(58) Field of Classification Search
CPC ... G01N 2035/0462; G01N 2035/0494; G01N 35/00871; G01N 35/0095; G01N 35/0099; G01N 35/021; G01N 35/04; G01N 35/1011; Y10T 436/11; Y10T 436/113332; Y10T 436/115831; Y10T 436/12
USPC ............ 436/43, 47, 50, 55, 164, 180, 501; 422/63, 65, 67, 82.05, 509, 521; 414/222.02
See application file for complete search history.

(56) References Cited

U.S. PATENT DOCUMENTS

| | | |
|---|---|---|
| 4,925,630 A | 5/1990 | Grunwald |
| 5,270,210 A | 12/1993 | Weyrauch et al. |
| 5,939,326 A | 8/1999 | Chupp et al. |
| 6,072,570 A | 6/2000 | Chipman et al. |
| 6,878,341 B2 | 4/2005 | Kowallis et al. |
| 6,937,955 B2 | 8/2005 | Barnes |
| 7,111,374 B2 | 9/2006 | Stewart |
| 7,457,686 B2 | 11/2008 | Ding et al. |
| 9,316,659 B2 * | 4/2016 | Dumitrescu ........... G01N 35/04 |
| 2002/0164808 A1 | 11/2002 | Itaya et al. |
| 2009/0117620 A1 * | 5/2009 | Fritchie ............... B01L 3/5085 435/91.1 |
| 2009/0193696 A1 | 8/2009 | Golabek, Jr. et al. |
| 2009/0210083 A1 | 8/2009 | English et al. |
| 2010/0034701 A1 * | 2/2010 | Pedrazzini ............ G01N 35/04 422/65 |
| 2015/0140668 A1 * | 5/2015 | Mellars ........... G01N 35/00871 436/50 |
| 2015/0241458 A1 * | 8/2015 | Pollack ........... G01N 35/00623 700/230 |

* cited by examiner

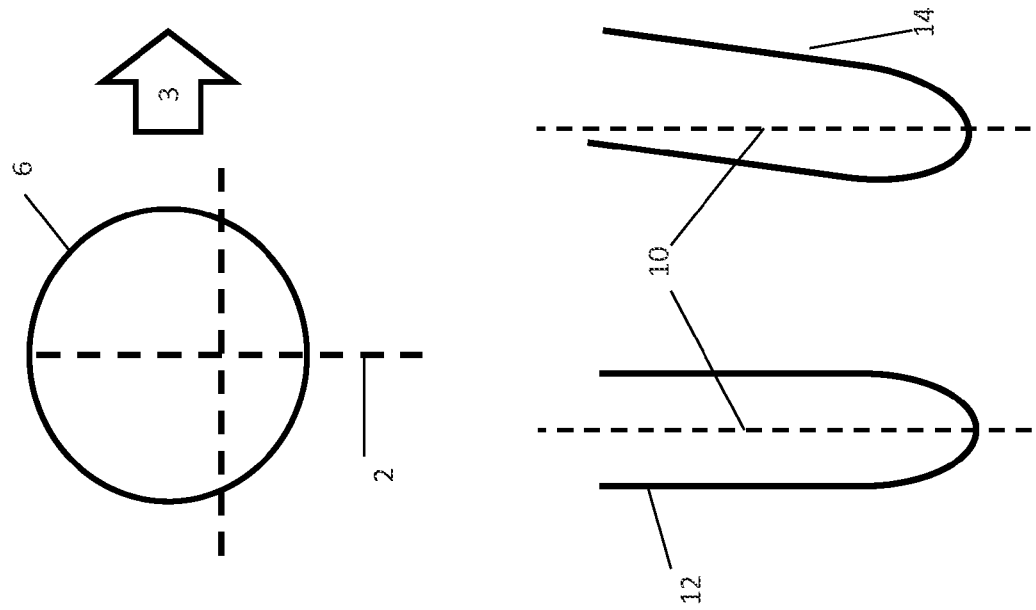
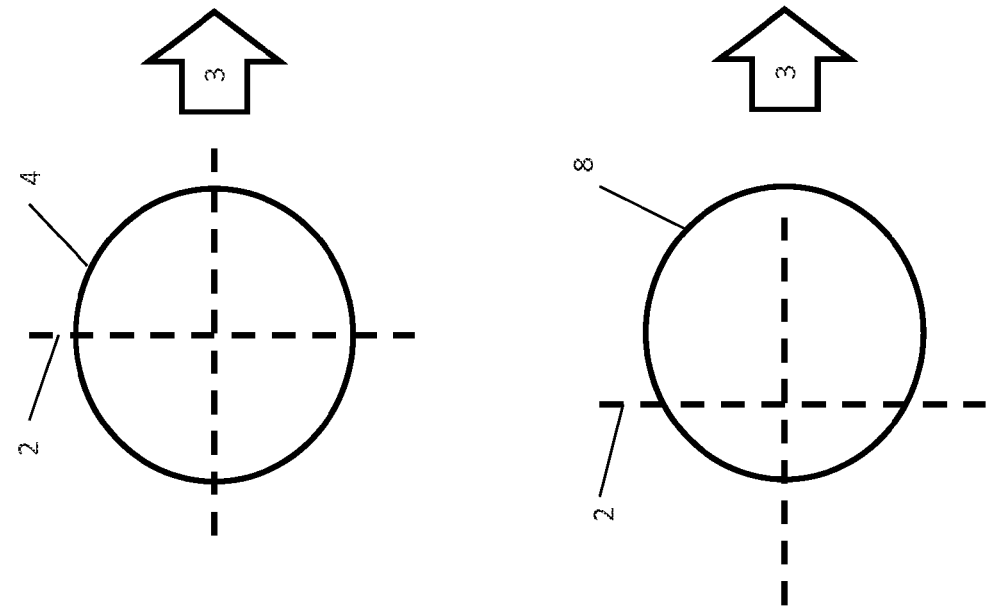
FIG. 1

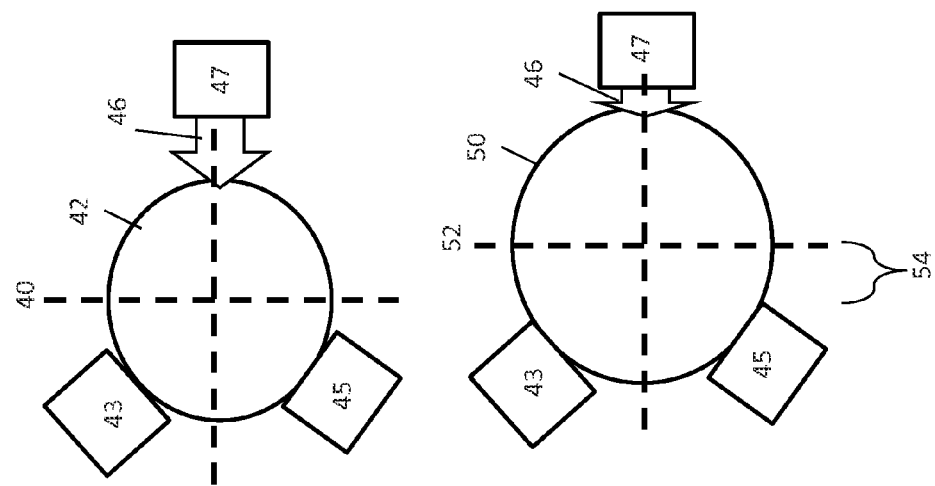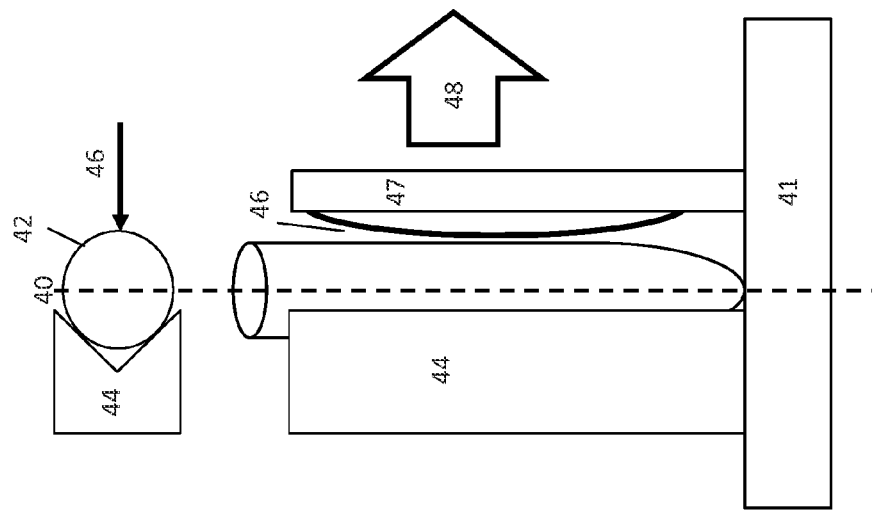
FIG. 3

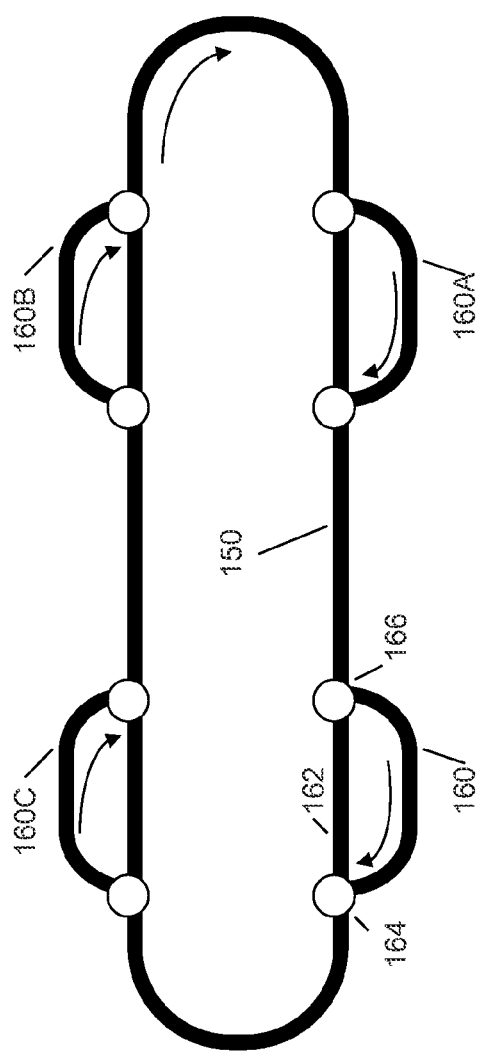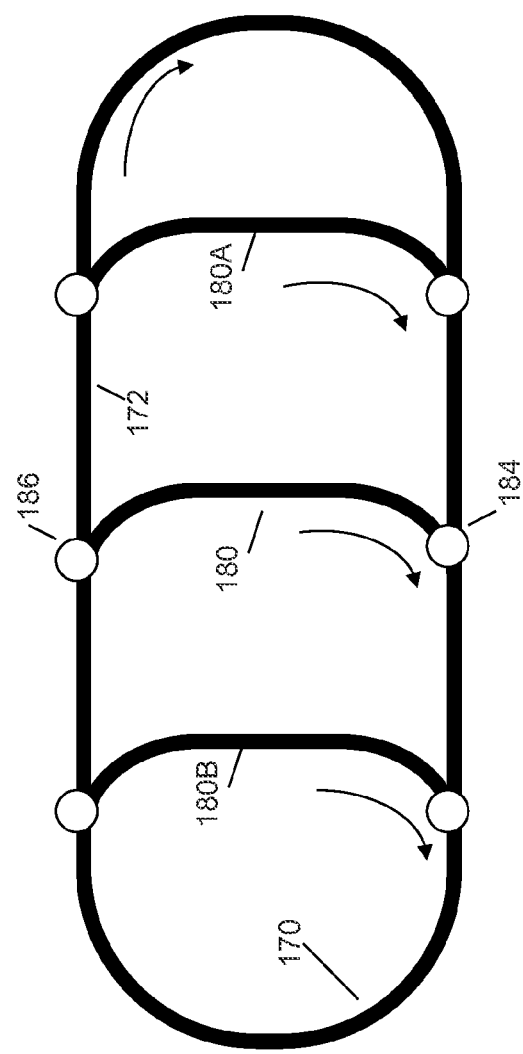

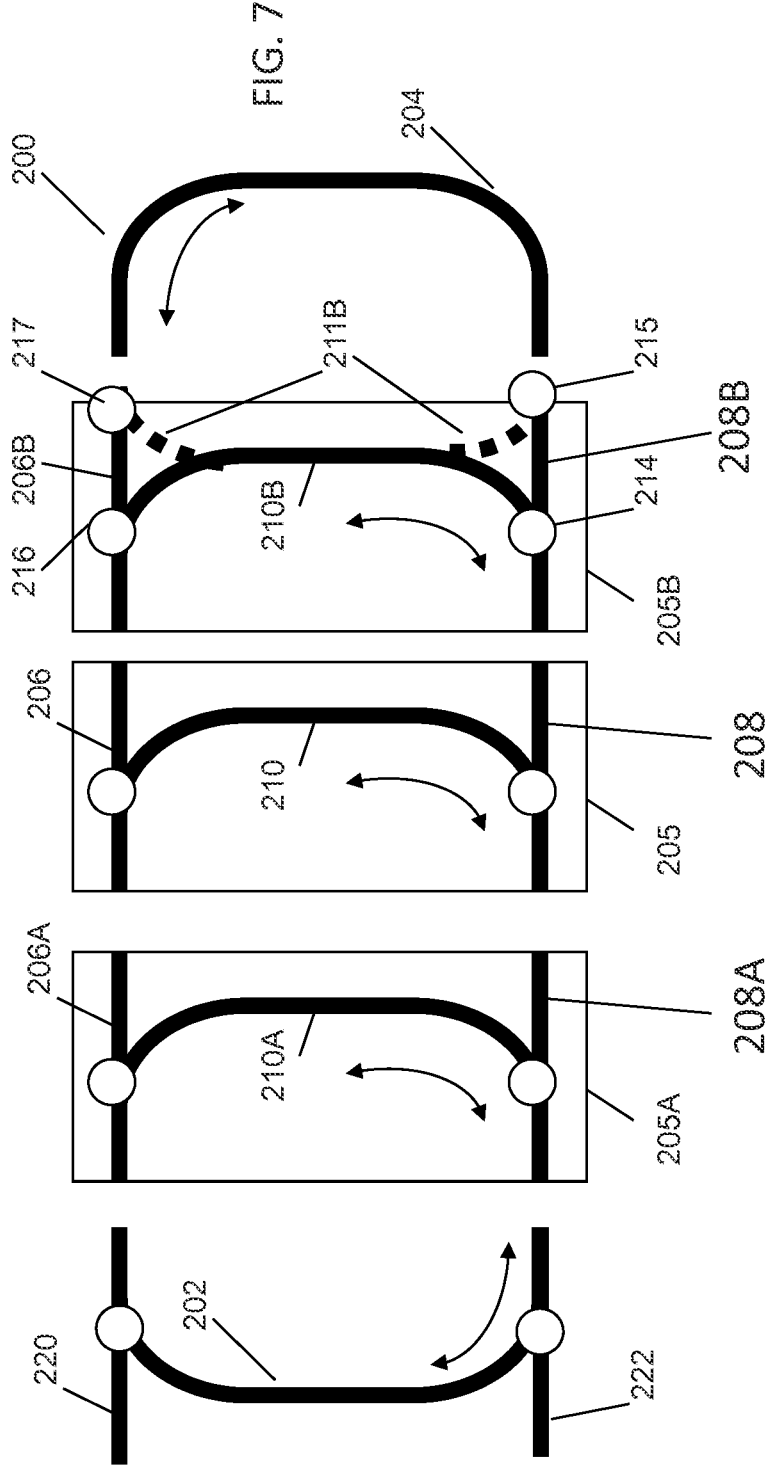

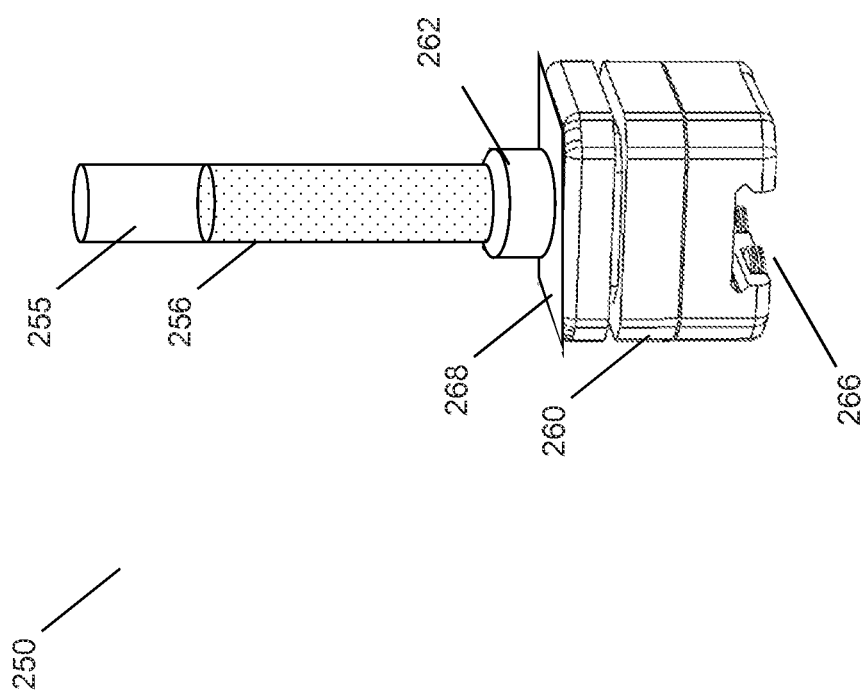

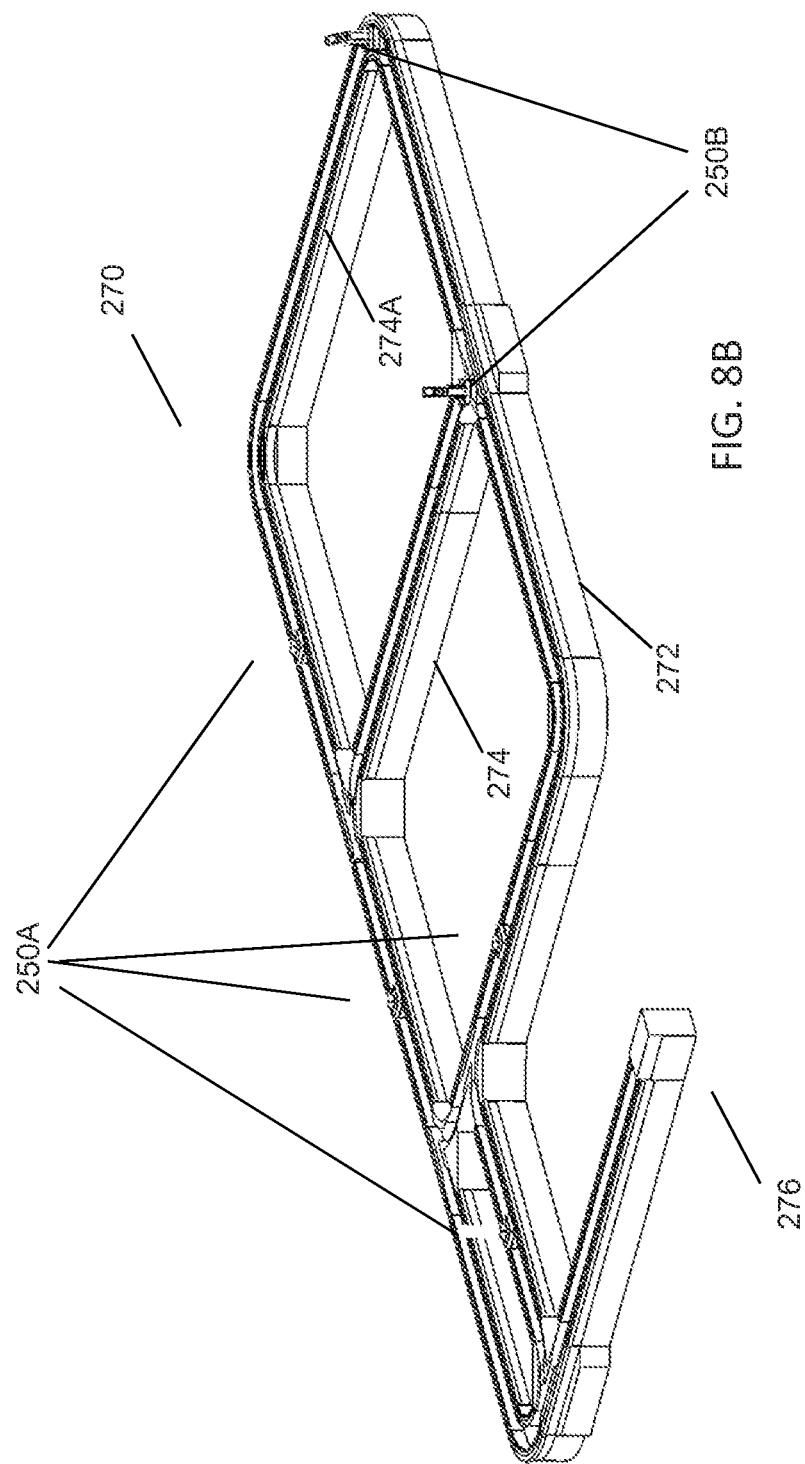

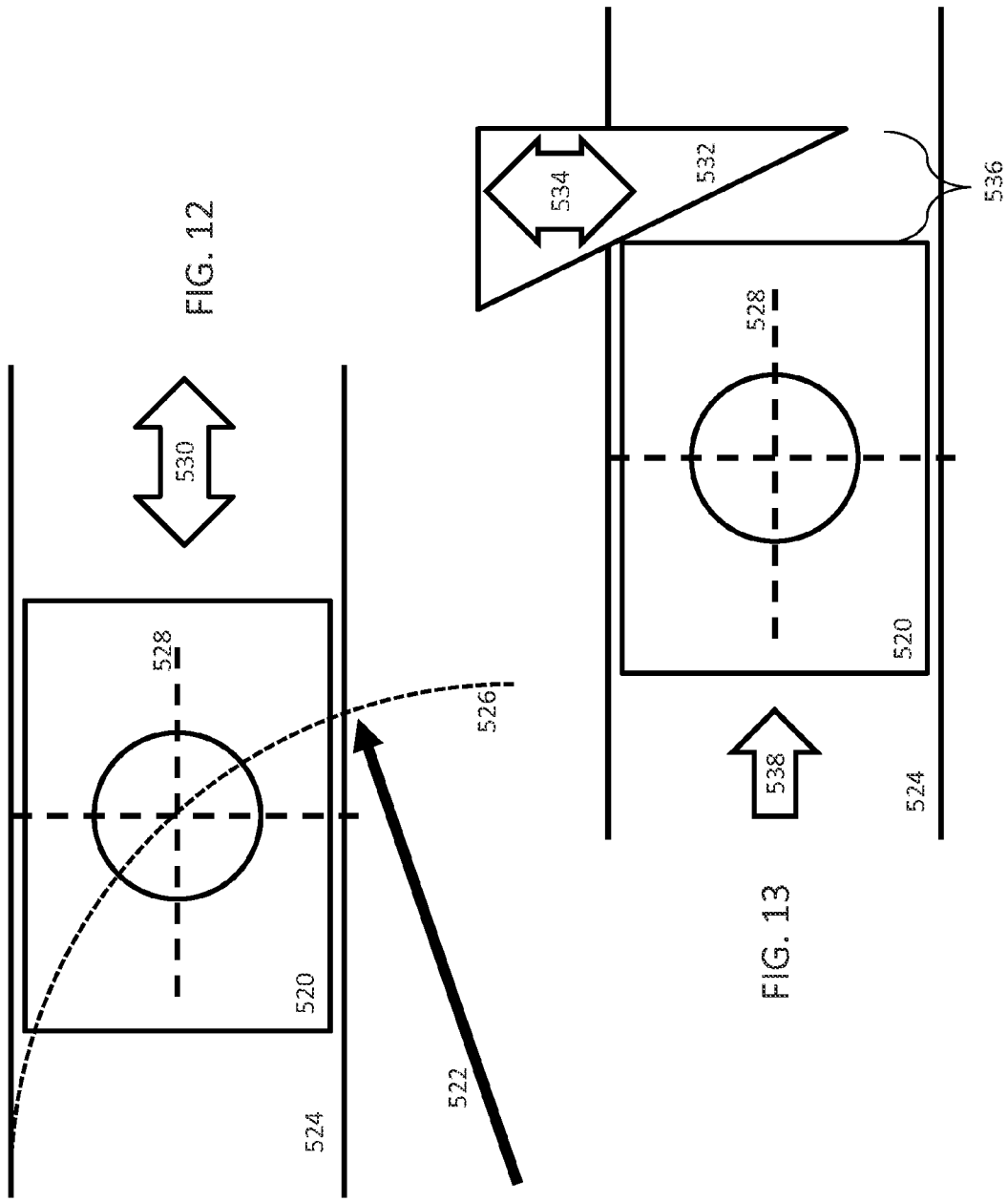

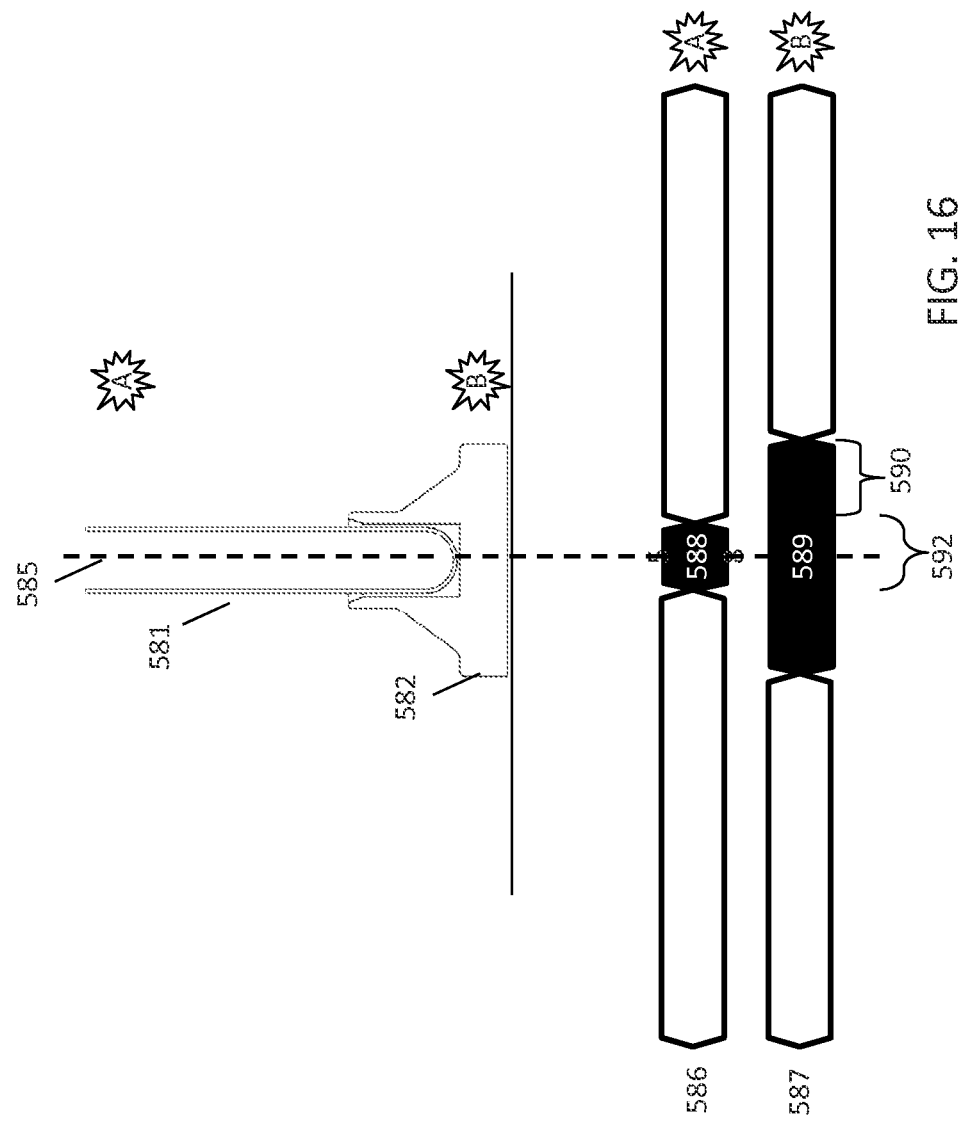

AUTOMATION TUBE POSITIONING METHODOLOGY

CROSS-REFERENCE TO RELATED APPLICATIONS

This application claims priority to U.S. provisional application Ser. No. 61/752,861 filed Jan. 15, 2013, which is incorporated herein by reference in its entirety.

TECHNOLOGY FIELD

The present invention relates in general to an automation system for use in a laboratory environment and, more particularly to systems and methods for transporting patient samples for in vitro diagnostics in a clinical analyzer and aligning sample vessels within an analyzer. Embodiments of the present invention are particularly well suited, but in no way limited to, systems and methods for accurately positioning carriers by characterizing them to determine a nominal stopping location.

BACKGROUND

In vitro diagnostics (IVD) allows labs to assist in the diagnosis of disease based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with automated clinical chemistry analyzers (analyzers) onto which fluid containers, such as tubes or vials containing patient samples have been loaded. The analyzer extracts a liquid sample from sample vessels and combines the sample with various reagents in special reaction cuvettes or tubes (referred to generally as reaction vessels). In some conventional systems, a modular approach is used for analyzers. A lab automation system can shuttle samples between one sample processing module (module) and another module. Modules may include one or more stations, including sample handling stations and testing stations (e.g., a unit that can specialize in certain types of assays or can otherwise provide testing services to the larger analyzer, which may include immunoassay (IA) and clinical chemistry (CC) stations.

An automation system for use with analyzers in an IVD environment moves tubes containing sample specimens between different stations within an analyzer or between analyzers. One common way to move these samples is by using passive carriers, such as pucks, along a friction track. Commonly, these automation tracks do not provide a large degree of precision when positioning samples. For example, passive pucks may be singulated and positioned mechanically using hard stops within the track. Singulation prongs may hold a puck in place once the puck has traversed the automation track to approximately the needed location. However, these prongs may not be adjustable for each puck and positioning a puck at a hard stop may not necessarily cause samples carried by the pucks to be repeatably positioned relative to instruments, such as pipettes, along the automation track.

While hard stops may be used to position a puck with relative repeatability, devices which interact with the sample, such as pipettes, may require precise orientation and positioning of the sample at a given location on the track. The position and orientation of each sample may vary relative to the hard stops from puck to puck. For example, the manufacturing tolerances between two pucks may prevent a repeatable location of the bottom of the tube relative to a given singulation point. In addition, tubes may shift within the grasp of a puck, such as by tilting, or moving off center from a holding location within the puck as the puck traverses the automation or at the time an operator places the tube into the puck.

One common way to provide somewhat repeatable positioning of a sample tube relative to a surface of a puck engages a singulation point using a holder having self-centering springs. A self-centering spring mechanism can include three or more springs that provide horizontal forces relative to one another to engage the walls of a sample tube to hold the tube approximately in the center of the mechanism. Self-centering springs may be expensive to manufacture with the tolerances necessary to provide self-centering action. For example, in designs where self-centering springs include multiple springs that push relative to one another, the self-centering action requires the relative forces of the springs to be approximately equal. Furthermore, self-centering springs may only be designed to allow tubes with a relative range of sizes that may be narrower than desired. Self-centering springs may also be poorly suited for maintaining the position of a tube while undergoing large forces as the puck travels around an automation track. The springs may also be poorly suited for preventing a sample tube from tilting at insertion or while traversing an automation track. Accordingly, self-centering springs alone may be an expensive or inadequate solution to repeatably position a sample tube with respect to a known point on a track.

SUMMARY

Embodiments of the present invention may address and overcome one or more of the above shortcomings and drawbacks by providing devices and systems for transporting samples using intelligent carriers that can be partially or substantially autonomous. This technology is particularly well-suited for, but by no means limited to, transport mechanisms in an automation system for use in an in vitro diagnostics (IVD) environment.

Embodiments of the present invention are generally directed to methods and systems for characterizing sample vessels and carriers in an automation system to determine any physical deviation from nominal positions. In response, an offset can be calculated and applied when positioning a carrier relative to a station, such as a testing or processing stations (or vice versa). This may allow for precise operation of an instrument with a sample vessel on an automation track, while compensating for manufacturing and other tolerances.

According to one embodiment of the invention, a method for aligning a sample vessel in an automation system in an IVD environment includes steps of measuring at least one distance between a reference point in a carrier and a position of a vessel within the carrier and automatically determining, using a processor, an offset associated with the vessel position. The methods further includes moving the carrier to a station within the analyzer for interaction between a sample contained in the vessel and a station and positioning the carrier at a location relative to the station responsive to the offset.

In one aspect of some embodiments, the method can include aspirating a portion of the sample using a pipette once the carrier has stopped. In another aspect of some embodiments, the step of measuring the distance can include observing the carrier and vessel with at least one camera or observing the carrier and the vessel using an LED and an electro-optical device. In another aspect of some embodiments, the steps of measuring and automatically determining an offset can be repeated when another vessel is inserted into the carrier. In yet another aspect of some embodiments, the method can include calibrating a line of action of the station or calibrating a station that performs the measuring step using a reference carrier prior to performing the measuring step. In still another aspect of some embodiments, the method can include calibrating the carrier using a station that performs the measuring step, prior to performing the measuring step.

According to another embodiment of the invention, a method for aligning a sample vessel in an automation system in an IVD environment includes steps of observing a sample vessel carried by a carrier to compare a location of the sample vessel to an expected location and automatically determining, using a processor, an offset associated with the vessel position. The method further includes moving the carrier along an automation track to a processing station within the analyzer for interaction between a sample contained in the vessel and a station and positioning the carrier at a location relative to the station responsive to the offset.

In one aspect of some embodiments, the step of observing can include observing the carrier and vessel with at least one camera or comparing an image of the sample to a pixel mapping of the expected location of the vessel in the image. The steps of observing and automatically determining an offset can be repeated when another vessel is inserted into the carrier. In another aspect of some embodiments, the step of observing can be performed by a characterization station located on the automation track. In yet another aspect of some embodiments, the step of positioning the carrier includes positioning the carrier such that the centerline of the vessel is substantially coincident with an arc of a pipette.

According to another embodiment of the invention, an automation system for use with a clinical chemistry analyzer includes an automation track configured to facilitate moving a plurality of carriers holding samples between a plurality of stations and a characterization station configured to observe sample vessels in plurality of carriers on the automation track and communicate observation information to at least one processor. The at least one processor can be configured to determine an offset corresponding to the centerline of each sample from the information received from the characterization station and facilitate stopping each corresponding carrier at a position determined by the offset to substantially align the centerline of each sample with a predetermined position in a station in the analyzer.

In one aspect of some embodiments, each carrier is configured to hold each sample vessel substantially vertically by applying a spring force to hold each sample against at least one vertical tine. Each carrier may be further configured to utilize a plurality of vertical tines to hold each sample vessel in substantially the transverse center of at least two tines. In another aspect of some embodiments, the processor is further configured to facilitate stopping each carrier such that the centerline of the vessel is substantially coincident with an arc of a pipette. In yet another aspect of some embodiments, the characterization station comprises at least one electro-optical device configured to capture an image of each vessel or at least one electro-optical device configured to detect when a sample vessel passes the electro-optical device. In still another aspect of some embodiments, the station includes an instrument having a pipette or a sample processing station.

According to another embodiment of the invention, a method for aligning a sample vessel in an automation system in an IVD environment includes steps of observing a sample vessel carried by a carrier to compare a location of the sample vessel to an expected location and automatically determining, using a first processor, an offset associated with the vessel position. The method further includes moving the carrier along an automation track to a processing station within the analyzer for interaction between a sample contained in the vessel and a station, stopping the carrier at a predetermined location at the processing station, and positioning an interaction device at a location relative to the carrier responsive to the offset.

In one aspect of some embodiments, the interaction device is a pipette or a robot arm. In another aspect of some embodiments, the step of positioning the interaction device occurs responsive to the control of a second processor in communication with the first processor. In yet another aspect of some embodiments, the offset includes a lateral component relative to the automation track, and the step of positioning the interaction device includes laterally positioning the interaction device responsive to the offset.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures:

FIG. 1 is a diagrammatical view of various types of positioning errors that may be corrected with some embodiments;

FIG. 3 is a top and side view of an exemplary carrier for use with some embodiments;

FIGS. 6A and 6B are diagrammatic views of track geometries that can be used with the automation system embodiments disclosed herein;

FIG. 7 is a diagrammatic view of an exemplary modular track configuration that can be used with the embodiments disclosed herein;

FIG. 8A is a perspective view of an exemplary carrier that can be used with the embodiments disclosed herein;

FIG. 8B is a perspective view of an exemplary track configuration that can be used with the embodiments disclosed herein;

FIG. 12 is a top view of an exemplary positioning scenario for use with some embodiments;

FIG. 13 is a top view of an exemplary positioning scenario for use with some embodiments;

FIG. 16 is a diagrammatic view of an exemplary characterization scenario for use with some embodiments;

DETAILED DESCRIPTION OF ILLUSTRATIVE EMBODIMENTS

Figure 2:
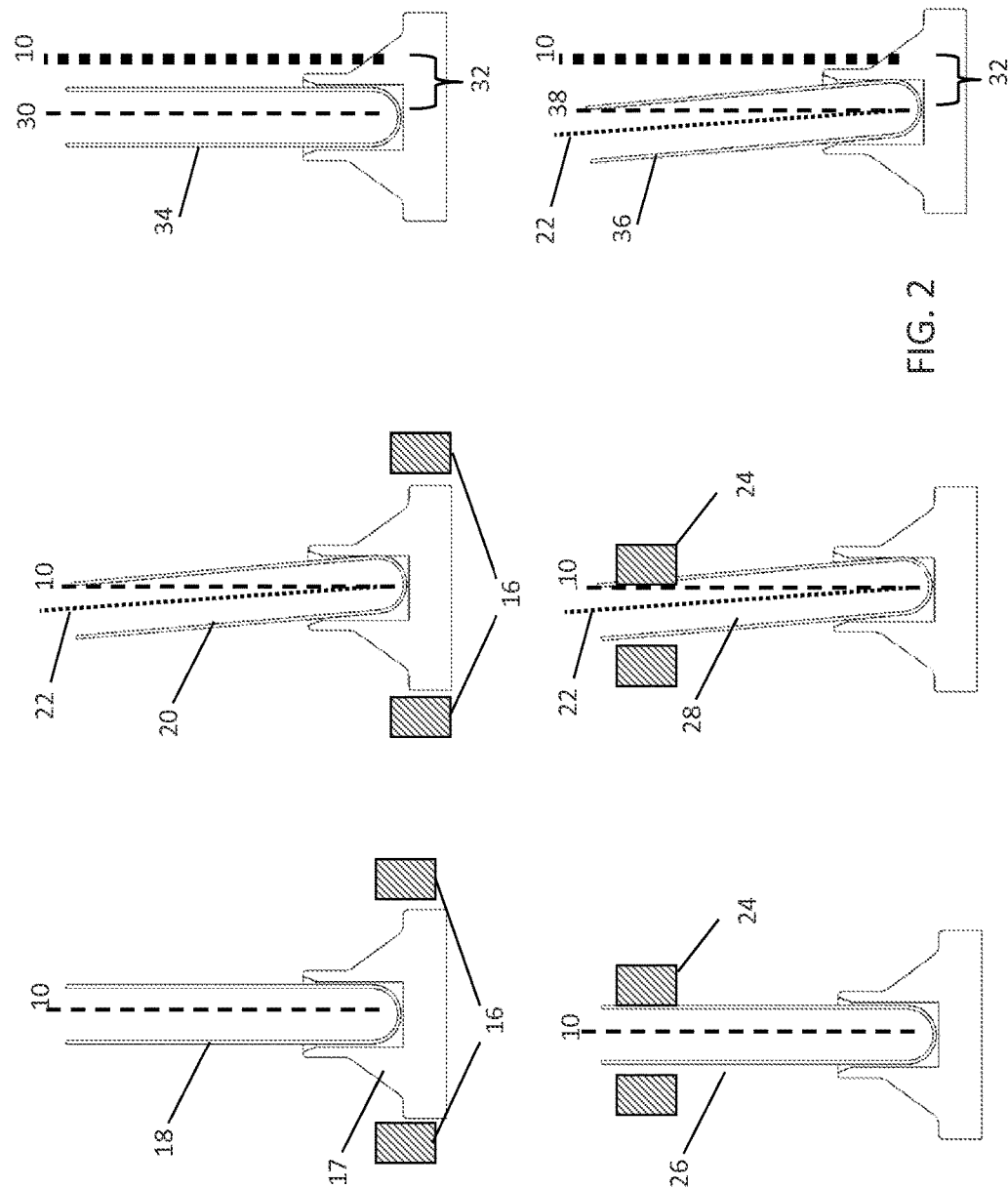
FIG. 2 is a diagrammatical view of various types of positioning errors that may be corrected with some embodiments.

Terms and Concepts Associated with Some Embodiments

Analyzer: Automated clinical analyzers ("analyzers") include clinical chemistry analyzers, automated immunoassay analyzers, or any other type of in vitro diagnostics (IVD) testing analyzers. Generally, an analyzer performs a series of automated IVD tests on a plurality of patient samples. Patient samples may be loaded into an analyzer (manually or via an automation system), which can then perform one or more immunoassays, chemistry tests, or other observable tests on each sample. The term analyzer may refer to, but is not limited to, an analyzer that is configured as a modular analytical system. A modular analytical system includes an integrated and extendable system comprising any combinations of a plurality of modules (which can include the same type of module or different types of modules) interconnected in a linear or other geometric configuration by an automation surface, such as an automation track. In some embodiments, the automation track may be configured as an integral conveyance system on which independent carriers are used to move patient samples and other types of material between the modules. Generally, at least one module in a modular analytical system is an analyzer module. Modules may be specialized or made redundant to allow higher throughput of analytical tasks on patient samples.

Analyzer module: An analyzer module is a module within a modular analyzer that is configured to perform IVD tests, such as immunoassays, chemistry tests, or other observable tests on patient samples. Typically, an analyzer module extracts a liquid sample from a sample vessel and combines the sample with reagents in reaction cuvettes or tubes (referred to generally as reaction vessels). Tests available in an analyzer module may include, but are not limited to, a subset of electrolyte, renal or liver function, metabolic, cardiac, mineral, blood disorder, drug, immunoassay, or other tests. In some systems, analyzer modules may be specialized or made redundant to allow higher throughput. The functions of an analyzer module may also be performed by standalone analyzers that do not utilize a modular approach.

Carrier: A carrier is a transportation unit that can be used to move sample vessels (and, by extension, fluid samples) or other items in an automation system. In some embodiments, carriers may be simple, like traditional automation pucks (e.g., passive devices comprising a holder for engaging a tube or item, a friction surface to allow an external conveyor belt in the automation track to provide motive force, and a plurality of sides that allow the puck to be guided by walls or rails in the automation track to allow the track to route a puck to its destination). In some embodiments, carriers may include active components, such as processors, motion systems, guidance systems, sensors, and the like. In some embodiments, carriers can include onboard intelligence that allows carriers to be self-guided between points in an automation system. In some embodiments, carriers can include onboard components that provide motive forces while, in others, motive forces may be provided by an automation surface, such as a track. In some embodiments, carriers move along automation tracks that restrict motion to a single direction (e.g., fore and aft) between decision points. Carriers may be specialized to a given payload in an IVD environment, such as having a tube holder to engage and carry a sample tube, or may include mounting surfaces suitable to carry different items around an automation system. Carriers can be configured to include one or more slots (e.g., a carrier may hold one or a plurality of sample vessels).

Central controller or processor: A central controller/processor (which may sometimes be referred to as a central scheduler) is a processor that is part of the automation system, separate from any processors onboard carriers. A central controller can facilitate traffic direction, scheduling, and task management for carriers. In some embodiments, a central controller can communicate with subsystems in the automation system and wirelessly communicate with carriers. This may also include sending trajectory or navigational information or instructions to carriers and determining which carriers should go where and when. In some embodiments, local processors may be responsible for managing carriers on local track sections, such as managing local queues. These local processors may act as local equivalents to central controllers.

Decision point: Decision points are points on an automation track where different navigational or trajectory decisions may be made for different carriers. A common example includes a fork in a track. One carrier may proceed without turning, while another may slow down and turn. Decision points may include stopping points at instruments, where some carriers may stop, while others may proceed. In some embodiments, deceleration zones ahead of turns may act as decision points, allowing carriers that will be turning to slow down to limit lateral forces, while others may proceed if not turning or if the motion profile for that carrier does not require slowing down. The decisions made at decision points can be made by processors onboard carriers, processors local to the track section, a central processor, or any combination thereof, depending on the embodiment.

Independent carrier: In some embodiments, carriers may be characterized as independently controlled carriers. Independently controlled carriers, are carriers with independently controlled trajectories. In some embodiments, independent carriers may be operating at the same time, on the same track, with carriers carrying one or a plurality of combinations of payloads that differ by size, weight, form factor, and/or content. The trajectories of each independently controlled carrier may be limited by a motion profile that includes maximum jerk, acceleration, direction, and/or speed for the carrier while moving in the automation system. The motion profile can limit or define the trajectory for each carrier independently. In some embodiments, a motion profile can be different for different sections of the automation system (e.g., in straight track sections vs. around curves to account for the added lateral forces while turning), for different carrier states (e.g., an empty carrier may have a different motion profile from a carrier transporting a sample or from a carrier transporting a reagent or other item), and/or for different carriers. In some embodiments, carriers can include onboard propulsion components that allow individual carriers to independently operate responsive to a motion profile or trajectory or destination instructions intended for each separate carrier.

Intelligent carrier/semi-autonomous carriers: In some embodiments, carriers may be characterized as intelligent carriers. An intelligent carrier is a carrier with onboard circuits that participates in motion, routing, or trajectory decisions. An intelligent carrier can include digital processors that execute software instructions to proceed along an automation surface responsive to the instructions or onboard analog circuits that respond to motion input (e.g., line follower circuits). Instructions may include instructions characterizing motion profiles, traffic, or trajectory rules. Some intelligent carriers may also include onboard sensors to assist onboard processors to route the carrier or make decisions responsive to the carrier's environment. Some intelligent carriers may include onboard components, such as motors or magnets, which allow the carrier to move responsive to control of an onboard processor.

In vitro diagnostics (IVD): In vitro diagnostics (IVD) are tests that can detect diseases, conditions, infections, metabolic markers, or quantify various constituents of bodily materials/fluids. These tests are performed in laboratory, hospital, physician office, or other health professional settings, outside the body of a patient. IVD testing generally utilizes medical devices intended to perform diagnoses from assays in a test tube or other sample vessel or, more generally, in a controlled environment outside a living organism. IVD includes testing and diagnosis of disease or quantifying various constituents of bodily materials/fluids based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with analyzers into which tubes or vials containing patient samples have been loaded. IVD can refer to any subset of the IVD functionality described herein.

Landmarks: In embodiments where carriers include onboard sensors, optical or other marks in track surfaces or locations viewable/sensible from track surfaces can act as landmarks. Landmarks can convey geographic information to carriers, such as a current location, upcoming stopping location, decision point, turn, acceleration/deceleration points, and the like.

Lab automation system: Lab automation systems include any systems that can automatically (e.g., at the request of an operator or software) shuttle sample vessels or other items within a laboratory environment. With respect to analyzers, an automation system may automatically move vessels or other items to, from, amongst, or between stations in an analyzer. These stations may include, but are not limited to, modular testing stations (e.g., a unit that can specialize in certain types of assays or can otherwise provide testing services to the larger analyzer), sample handling stations, storage stations, or work cells.

Module: A module performs specific task(s) or function(s) within a modular analytical system. Examples of modules may include: a pre-analytic module, which prepares a sample for analytic testing, (e.g., a decapper module, which removes a cap on top of a sample test tube); an analyzer module, which extracts a portion of a sample and performs tests or assays; a post-analytic module, which prepares a sample for storage after analytic testing (e.g., a recapper module, which reseals a sample test tube); or a sample handling module. The function of a sample handling module may include managing sample containers/vessels for the purposes of inventory management, sorting, moving them onto or off of an automation track (which may include an integral conveyance system, moving sample containers/vessels onto or off of a separate laboratory automation track, and moving sample containers/vessels into or out of trays, racks, carriers, pucks, and/or storage locations.

Payload: While exemplary carriers are described with respect to carrying patient samples, in some embodiments, carriers can be used to transport any other reasonable payload across an automation system. This may include fluids, fluid containers, reagents, waste, disposable items, parts, or any other suitable payloads.

Processor: A processor may refer to one or more processors and/or related software and processing circuits. This may include single or multicore processors, single or multiple processors, embedded systems, or distributed processing architectures, as appropriate, for implementing the recited processing function in each embodiment.

Pullouts, sidecars, offshoot paths: These terms may be used to refer to track sections that are off the main portion of a track system. Pullouts or sidecars may include chords, parallel tracks, or other suitable means for separating some carriers from a primary traffic pattern. Pullouts or sidecars may be configured to facilitate physical queues or allow certain carriers to stop or slow down without disrupting traffic on a main track section.

Samples: Samples refers to fluid or other samples taken from a patient (human or animal) and may include blood, urine, hematocrit, amniotic fluid, or any other fluid suitable for performing assays or tests upon. Samples may sometimes refer to calibration fluids or other fluids used to assist an analyzer in processing other patient samples.

STAT (short turnaround time) sample: Samples may have different priority assigned by a laboratory information system (LIS) or operator to assign STAT priority to samples that should take precedent over non-STAT samples in the analyzer. When used judiciously, this may allow certain samples to move through the testing process faster than other samples, allowing physicians or other practitioners to receive testing results quickly.

Station: A station includes a portion of a module that performs a specific task within a module. For example, the pipetting station associated with an analyzer module may be used to pipette sample fluid out of sample containers/vessels being carried by carriers on an integrated conveyance system or a laboratory automation system. Each module can include one or more stations that add functionality to a module.

Station/module: A station includes a portion of an analyzer that performs a specific task within an analyzer. For example, a capper/decapper station may remove and replace caps from sample vessels; a testing station can extract a portion of a sample and perform tests or assays; a sample handling station can manage sample vessels, moving them onto or off of an automation track, and moving sample vessels into or out of storage locations or trays. Stations may be modular, allowing stations to be added to a larger analyzer. Each module can include one or more stations that add functionality to an analyzer, which may be comprised of one or more modules. In some embodiments, modules may include portions of, or be separate from, an automation system that may link a plurality of modules and/or stations. Stations may include one or more instruments for performing a specific task (e.g., a pipette is an instrument that may be used at an immunoassay station to interact with samples on an automation track). Except where noted otherwise, the concepts of module and station may be referred to interchangeably.

Tubes/sample vessels/fluid containers: Samples may be carried in vessels, such as test tubes or other suitable vessels, to allow carriers to transport samples without contaminating the carrier surfaces.

Exemplary Embodiments

Embodiments of the present invention may overcome some of the shortcomings of the prior art by providing the ability to characterize the position of each sample tube relative to its carrier and by further providing the ability to calculate an offset that should be applied to the stopping location of each carrier, such that the sample tube may be placed with a desired precision at a station serviced by an automation track. In some embodiments, carriers may be provided that do not rely on hard singulation stops to come to rest at a desired stopping location. These carriers may further include the ability to precisely stop at a desired offset from an absolute stopping location, allowing a sample tube to be positioned independently of a hard stop. By characterizing the location of the sample relative to a carrier and positioning a carrier relative to an offset calculated from this characterization, a sample tube may be precisely and reliably positioned relative to instruments or sample processing stations (which together may generally be referred to as stations), such as pipettes, sample handling stations, or decappers/recappers, that may require reliable positioning of samples prior to operation. Furthermore, in some embodiments, a wide range of tube sizes may be used, and an offset may be used to reliably position the center of each sample tube relative to an instrument.

In the prior art, hard stops were used to determine the stopping location of a carrier, such as a puck. However, the position and orientation of sample tubes may vary between carriers relative to the position of the hard stop. As a result, the resting position orientation of a sample tube may vary from a nominal position. There are three primary ways in which the position and orientation of a sample tube may vary from a nominal position as shown in FIG. 1. FIG. 1 shows the relative position of a line of action to the walls of the sample tube. A line of action can be considered the path that a probe tip will take when interacting with a tube. A line of action may be represented by crosshairs (such as line of action 2) when viewing the horizontal plane in a top-down fashion or as a vertical line (such as line of action 10) when viewing of the line of action from the side. Positioning errors can be considered a deviation of the center of a tube relative to the line of action of an instrument in the horizontal plane, while tilt errors can be considered deviations of the center of a tube relative to the line of action from the side.

Tube 4 shows an ideal position (i.e., nominal) where the center of tube 4 coincides with the line of action 2. Tube 4 travels in a direction 3, along an automation track. In this example, tube 4 has come to rest at a nominal position. Tube 6, however, is positioned with an error in the lateral direction from the nominal position of the line of action 2. Tube 8 is positioned with an error in the longitudinal direction (i.e., along the direction of travel 3) relative to the nominal position where the center of tube 8 would be coincident with line of action 2. Tubes 6 and 8 illustrate X and Y positional errors. Tubes may also be described as sample vessels, as some embodiments can work with various shaped sample vessels that may be used to transport samples in an IVD environment.

Tube 12 shows the ideal, nominal tilt of a tube relative to the line of action 10. Here, tube 12 is positioned in the nominal vertical direction. Tube 14 has a tilt error relative to the line of action 10, illustrating an extreme angle of tilt that may be experienced by a tube that is positioned at an instrument in an automation system. The positional errors of tubes 6 and 8 and the tilt error of tube 14 are not ideal and may make it difficult to operate an instrument. For example, a pipette may clip the wall of the sample tube interfering with its operation. Furthermore, if smaller tubes are used, it may be difficult or impossible for that tube to interact with an instrument due to the position or tilt errors illustrated in FIG. 1.

FIG. 2 illustrates the effect of using hard stops to position centers of tubes relative to lines of action. Hard stops 16 stop carrier 17 along an automation track at a predetermined location. Carrier 17 carries a tube, such as tube 18. Tube 18 illustrates a nominal position for the center of the tube relative to line of action 10, which may be the line of action of a pipette at a testing station. Tube 20, however, reveals a potential issue using hard stops 16 to stop a carrier at the base of the carrier 17. Center line 22 at the center of tube 20 is tilted relative to line of action 10. Therefore, tube 20 has a tilt error relative to nominal.

Hard stops 24 illustrate another potential issue using hard stops to position the stopping point of a tube. Engaging a tube using hard stops may also damage or jar a tube and may be problematic for any number of reasons other than introducing positional errors, such as risking tipping a carrier over, which may cause the contents of a sample tube to spill. Tube 26 engages hard stops 24 at a nominal position and orientation. The center of tube 26 is coincident with line of action 10. However, tube 28 comes to rest at a tilt relative to line of action 10. In some instances, tube 28 may be knocked into a tilted orientation due to the force used to stop the tube by hard stops 24. Center line 22 has a tilt error relative to the nominal position.

Tubes 34 and 36 illustrate how tubes may come to rest with a positional error relative to nominal that may be introduced by any number of causes. For example, the best line of action available for tube 34, which may be centerline 30, may deviate from the line of action 10 of an instrument by an offset 32. This offset 32 is a positional error. In this instance, a pipette operating along the line of action 10 will completely miss the contents of sample tube 34. Offset 32 may be introduced because carrier 17 stopped too soon, or because tube 34 is off center from the center of carrier 17. For example, carrier 17 may include a holding mechanism that is designed to operate with a plurality of different sizes of tubes. Larger tubes may result in a different location of the center of the tube compared to the center of a smaller tube. It should be appreciated that for smaller diameter tubes the likelihood that an offset 32 will be outside the diameter of the tube is increased. Accordingly, if smaller tubes or tube top cups are used, the offset 32 may require a smaller margin of error.

Tube 36 has a positional error as indicated by offset 32 between the nominal line of action 10 (e.g., the nominal resting position of tube 36) of an instrument and the nominal line of action 38 for tube 36. It should be noted that tube 36 also has a tilt error as indicated between the center line 22 and the nominal line of action for the tube, line 38. Line 38 indicates that a pipette could still be inserted into tube 36 to reach fluids contained in the tube, even though a tilt has been introduced. While this tilt may not be ideal because the range of positions that can be used for a line of action into the tube is limited, in some embodiments, the offset 32 can still be used to position the line of action of a pipette at a viable line of action within the tube by removing the offset.

FIG. 3 shows an exemplary embodiment of the tube carrier portion of a carrier that may be suitable for reducing tilt errors in the positioning of a tube. Tube 42 includes a centerline 40. Tube 42 is carried by carrier 41, which includes a V-shaped block 44 that allows tube 42 to be self-centered in the lateral direction when held in place by a force in the longitudinal direction, which may be provided by spring, such as leaf spring 46. Tine 47 may support leaf spring 46. Because of the V-shaped block 44, regardless of the diameter of tube 42, a force in the longitudinal direction can force the tube into the recess of the v-shaped block and orient the tube vertically at the lateral center point of the recess. Such a design can utilize a single spring 46 which may be a single strong spring which may hold tube 42 into block 44 with sufficient force that carrier 41 may undergo any reasonably desired range of acceleration while traversing the automation track without movement of tube 42. Furthermore, because only a single spring need provide a force, the tolerance needed in producing and selecting the spring may be very low. In contrast, many self-centering spring designs require various springs to provide competing forces, such that the springs must be tightly toleranced to provide balanced spring forces to ensure the tubes are held in the center. In a carrier 41, spring 46 works with block 44 to reliably center tube 42 in the lateral direction, but not necessarily in the longitudinal direction. Larger or smaller tubes may sit in block 44 with a center that moves fore or aft relative to carrier 41 when carrier 41 is oriented in a direction of travel 48.

Block 44 includes a V-shaped channel that is oriented in a vertical direction, forming a vertical spine. Because tubes generally have substantially parallel walls, a force pushing the tube into this V-shaped spine will generally orient the centerline of the two parallel walls to the orientation of the spine, as this is the lowest energy state and resting place of the tube within the V-shape. In this manner, block 44 may provide advantages over traditional self-centering spring designs. First, a sufficiently large force will keep tube 44 oriented in a substantially vertical direction, therefore minimizing or eliminating tilt errors in the orientation of the tube. Furthermore, even with a poorly toleranced spring 46, tube 44 will be substantially oriented at the center of block 44 in the lateral direction. Accordingly, carrier 41 need only be moved to a proper location in direction 48 to position tube 42 in substantially the nominal location for a line of action of a given instrument within an automation system.

Block 44 may be replaced with two tines 43 and 45 that provide a V-shaped recess into which a tube may be placed, while allowing the backside of the tube to be viewed. For example, the gap between tines 43 and 45 may allow viewing of any barcode information on tube 42. The gap between tines 43 and 47 and between tines 45 and 47 may also allow reading of any barcode information viewable on the sides of tube 42.

A larger tube 50 may also be placed between lines 43, 45, and 47. As can be seen in FIG. 3, the centerline 52 is moved in a fore direction relative to centerline 40 of tube 42. This is because the larger diameter of tube 50 causes tube 50 to sit further forward in the V shape of tines 43 and 45 and because the larger diameter causes the centerline to sit further from the points of contact with tines 43 and 45. Spring 46 is more compressed when holding larger tube 50. While centerline 52 is moved forward from centerline 40 by a distance 54 due to the difference in sizes of the tubes, it should be appreciated that both tube 42 and tube 50 are both oriented substantially parallel to tines 43 and 45 and centered in the lateral direction between tines 43 and 45. Accordingly, the distance 54 between the centerlines can be corrected by using a different offset when positioning carrier 41 at an instrument along the automation system to align the centerline of each instrument with the centerline of each tube.

Figure 4:
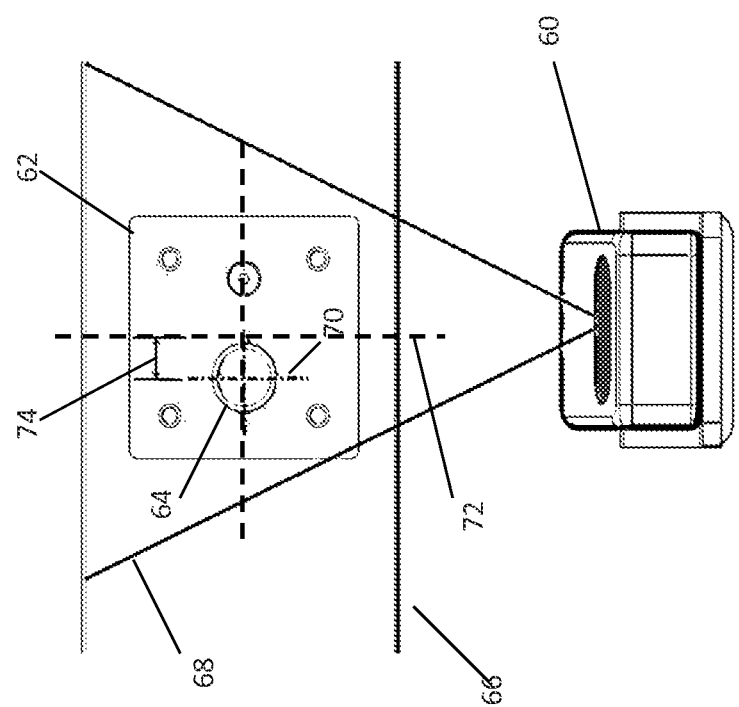
FIG. 4 is a top view of an exemplary characterization station for use with some embodiments.

FIG. 4 shows an exemplary characterization station that may be used to characterize offsets needed to position a tube at an optimal position on an automation track. The characterization station can include an optical measuring device 60 that measures the distances between tubes and carriers relative to some known or expected position on the carrier. The optical measuring device 60 can include any suitable optical measuring device, such as a camera that can characterize distances in an image (such as by mapping pixel distances relative to known distances in the real world). Other optical measuring devices can include a laser scanning or timing devices or any other optical device discussed herein that may be suitable for characterizing offsets between positions of tubes and nominal positions within the automation system.

Optical measuring device 60 can characterize carrier 62 and a tube 64 being carried by carrier 62. Carrier 62 travels along automation track 66, which may be any suitable automation track known in the art or disclosed herein. Optical measuring device 60 can measure distances within field of view 68. For example, optical measuring device 60 may project an infrared beam onto an object, allowing accurate measurements of the relative distances within the field of view. In some embodiments, optical measuring device 60 may include IR rangefinders or projection devices along with mono or stereoscopic cameras. This may allow the characterization station to measure distances in one dimension, two dimensions, or three dimensions.

In some embodiments, a raster scan or a single slice of a scan can be used to measure a single distance of a tube surface relative to a nominal position along the direction of travel. In some embodiments, one or more LEDs on one side of automation track 66 and an electro-optical device, such as a camera or one or more photo detectors on the other side of the track can provide precise timing-based measurement of shapes and distances between portions of objects passing along the track. For example, precise timing when the fore and aft portions of a carrier pass a characterization station, and when the fore and aft portions of a tube pass the characterization station, can provide precise information about the relative location of the tube within the carrier. In some embodiments, an overhead camera may be used, which may provide a two-dimensional image and allow for a two-dimensional, X-Y measurement of the position and orientation of a tube relative to a carrier. In some embodiments, multiple cameras may be used to provide two or three dimensional information of the position orientation of the tube within a carrier, as well as providing more image details for a more robust measurement of offsets of the tube from a nominal position.

In some embodiments, a light source may be used in conjunction with one or more cameras to allow illumination of tubes and carriers or to provide distinguishable colors or patterns that may be used to provide additional detail to an image. For example, an IR light source can be used with an IR camera to provide detail in an image that may not be otherwise available from ambient light. In some embodiments, a monochrome grid may be projected to assist in viewing depth in an image. Furthermore, in some embodiments, the IR beam and an IR camera can be used in conjunction with another visible-light camera (that may be offset from the IR camera) to provide color and range information.

In addition, the light source may be offset from the viewing camera, which may allow distance information to also be gathered from the image in some embodiments, the optical system used may be similar to the system used by the Xbox Kinect vision system available from Microsoft Corporation. In some embodiments, three-dimensional information is gathered by the use of a plurality of cameras and/or a plurality of light sources.

Optical measuring device 60 can measure a distance 74 between the observed centerline 70 of tube 64 and the expected centerline 72, which may coincide with the centerline or a known position relative to carrier 62. In some embodiments, a single carrier carries a single tube at the geometric center of the carrier in the longitudinal direction under nominal conditions. In some embodiments, a carrier may be configured to carry multiple tubes, include multiple tube slots that may be occupied, or otherwise include a non-central tube slot at a known location relative to a point on the carrier. Observing a distance 74 between the actual centerline of a tube and the expected centerline of the tube may identify an offset that should be applied to carrier 62 when carrying tube 64 for each station the carrier visits. The next time a tube is inserted into carrier 62, a new offset 74 can be determined during another characterization. In some embodiments, a carrier/tube combination is characterized at least once for each tube that is inserted into a carrier. In some embodiments, a tube and carrier combination may be characterized multiple times as it traverses an automation system.

The term characterization station, as used herein, is any combination of components in the automation system that calibrates distances between a position of a tube, such as the tube's centerline, relative to other positions within the automation system, such as the leading edge of a carrier or a part of the carrier that is used to provide a reference position. In some embodiments, carriers can include optical marks, such as opaque or reflective marks or patterns, physical surfaces, such as leading edges or indentations, magnetic devices, or any other identifiable points on a carrier that may be used for reference points in a distance measurement. In some embodiments, characterization stations perform measurements of tubes relative to reference points on a carrier using optical means, such as cameras or other optical devices disclosed herein. In some embodiments, characterization stations may observe and characterize carriers and tubes using other means, such as magnetic measurement or physical measurement, such as providing feelers to note the distances between surfaces of a tube and a carrier. In some embodiments, radiation devices, such as x-ray or tomography devices, may be used to measure positions of tubes and surfaces of carriers to characterize carriers and/or combinations of carriers and tubes.

Exemplary Automation System

Some embodiments may use systems and methods that provide a more efficient lab automation system to allow samples to be shuttled between and amongst various analyzer testing stations with less latency and more individual control. Exemplary systems can reduce or eliminate queues experienced by samples traversing the automation system. Samples may undergo many different types of testing in an ACA, which may not be available in a single testing station. Testing stations within an ACA can be adapted for specialized testing. For example, immunoassays may be performed by an immunoassay station that includes certain incubation capabilities and uses specific reagents that are unique to immunoassays. Chemical analysis can be performed by a clinical analyzer and electrolyte chemistry analysis can be conducted by an ion-selective electrode (ISE) clinical analyzer. By using this modular approach, an ACA can be adapted not only to the types of testing being done on samples, but also the frequency and volume of testing necessary to accommodate the needs of the lab. If additional immunoassay capability is needed, a lab may choose to add additional immunoassay stations and increase overall throughput for immunoassay testing in their system.

Figure 5:
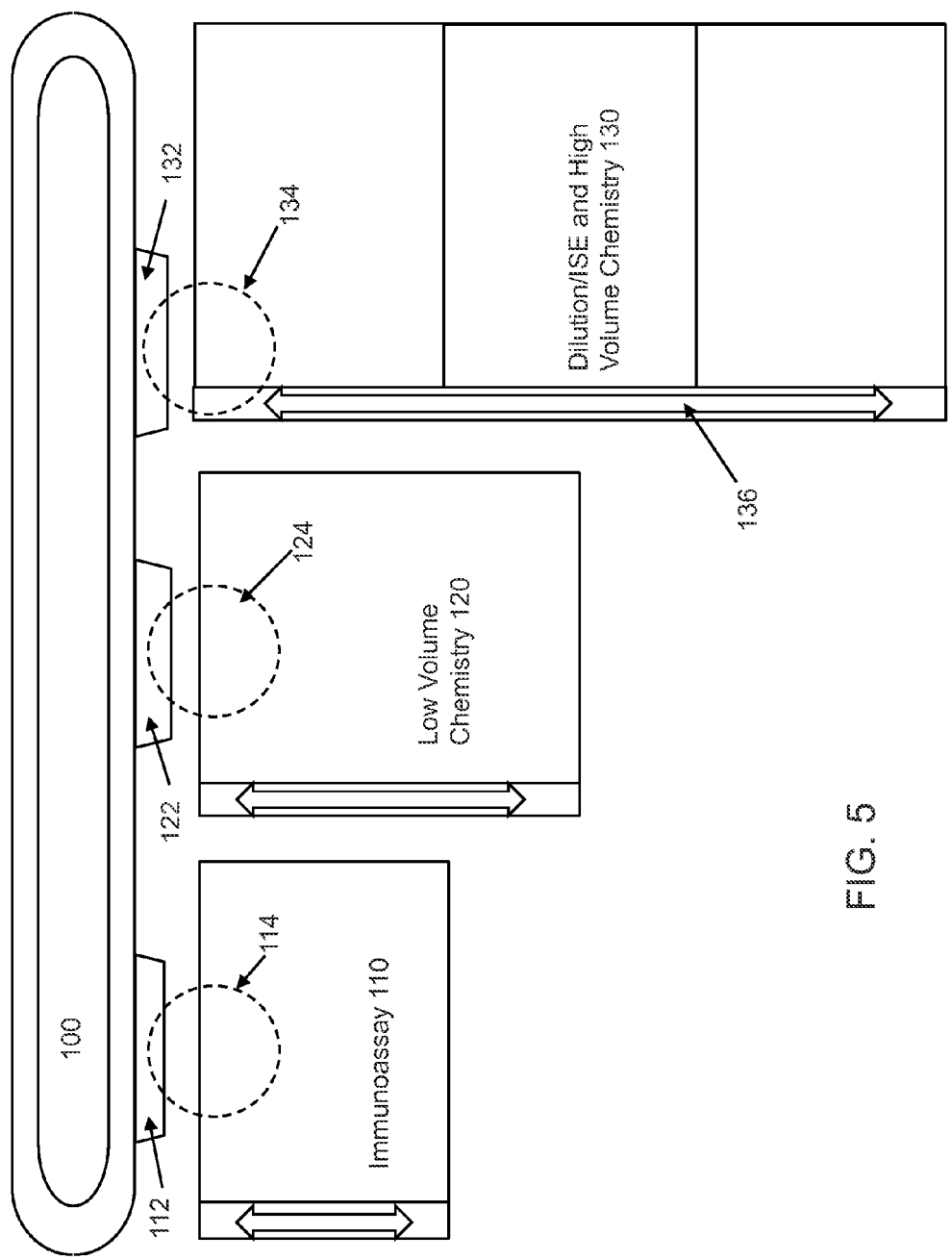
FIG. 5 is a top view of an exemplary clinical analyzer geometry that can be improved by use of the automation system embodiments disclosed herein.

An exemplary track geometry, for use in transporting samples within an analyzer typical in prior art configurations, is shown in FIG. 5. This track can include prior art friction tracks, which may introduce problems in designing a track system. However, certain embodiments of the present invention could also use a similar geometry without necessarily employing a friction track for motion. Track 100 can be a generally oval-shaped track that conveys samples in pucks or trays between various stations, such as sample preparation or analyzing/testing stations 110, 120, and 130. Track 100 could be a single direction track or, in some instances, a linear bidirectional track. In this exemplary set-up, each analyzer 110, 120, 130 is serviced by a respective sidecar 112, 122, 132. At the junction between the track 100 and each sidecar, a gate or switch can be placed that allows samples to be diverted to or from track 100 to the sidecar. The oval nature of track 100 can be used to circulate samples while they wait for access to each analyzer. For example, analyzer 110 may have a full queue in sidecar 112, such that new samples on track 100 cannot be diverted to pullout 112 until analyzer 110 finishes handling a pending sample in sidecar 112 and inserts it back into the main traffic flow of track 100.

In some systems, each sidecar can be serviced by a handling mechanism such as sample probe arms 114, 124, and 134. These robotic handling arms can aspirate sample material from samples in a sidecar via a probe needle, or can pick up a sample tube from the sidecar and transport it into the corresponding testing station. In this exemplary system, the available testing stations include an immunoassay station 110, a low-volume chemistry station 120, and an expandable dilution/ISE electrolyte and high-volume chemistry station (or stations) 130. Some advantages of this approach are that the track 100 can be part of a separate lab automation system that can be added onto otherwise self-contained stations, and the track 100 and stations 110, 120, and 130 can be independently upgraded, purchased, or serviced. Some stations, such as high-volume chemistry station 130, can include their own friction track 136 that operates independently of track 100. Friction track 136 can include a bidirectional friction track that allows samples to move between sub-modules of high-volume chemistry station 130. A drawback of this type of system may be that the separate friction tracks operate independently and, control of overall automation becomes more complicated. Furthermore, transitions between friction tracks 136 and 100 can be slow and cumbersome, particularly where there is no direct route between two friction tracks. In some systems, moving between tracks may require lifting and placing samples via a robot arm. In some embodiments, each automation track can include one or more characterization stations to provide characterization of the location and placement of each sample tube within each carrier, as the placement may change if the carrier is moved between automation tracks. In embodiments where a single track having different contiguous track sections is used, a single characterization may be sufficient. In some embodiments, multiple characterization stations are used to provide additional precision by increasing the number of measurements.

Some automation systems for analyzers can treat individual analyzer/testing stations as generic destinations for a sample on the track. In some embodiments, the lab automation system can be integrated within the individual testing stations, which can substantially reduce or eliminate the complexity of the individual testing stations and reduce the need for separate sample handling systems within each station. In some embodiments, by integrating the lab automation system into the stations, the system can begin to treat individual stations less as generic destinations and more as portions of a multi-route track onto which a sample can travel.

FIG. 6A shows one embodiment of a track system that can be adapted for use with the present invention. Track 150 is a rectangular/oval/circular track on which sample carriers move in a clockwise (or counterclockwise) direction. Track 150 may be unidirectional or bidirectional. Carriers can transport any suitable payload with an IVD environment, such as fluid samples, reagents, or waste. Fluids, such as patient samples can be placed in a container or vessel, such as a test tube, vial, cuvette, etc. that can be transported by a carrier. Carriers and, by extension payloads, such as samples, can move on the main track 150 or be diverted via decision points such as 164 or 166. These decision points can be mechanical gates or other mechanisms suitable for allowing a sample to be diverted from the main track 150 to a sidecar, such as 160, 160A, 160B, 160C as described herein. By way of example, if a sample carrier is traversing the main path 150 and reaches decision point 166, it can be made to continue on the main track to segment 162 or it can be made to divert to sidecar 160. The systems and methods by which the decision can be made to divert the sample carrier at decision point 166 are described throughout.

FIG. 6B shows an alternative track layout that may be suitable for certain embodiments of the present invention. Track 170 is also a generally circular track with sample carriers moving clockwise (or counterclockwise). In this example, rather than having sidecars outside of the track, pullouts 180, 180A, and 180B are chords within the track. Similarly, when sample carriers reach decision points, they may be diverted off of the main path to a side path such as path 180. At decision point 186, a sample on the main track 170 can be made to continue on the main track or be diverted onto path 180. Once an analyzer station along handling path 180 is done processing the sample, the sample proceeds to decision point 184 where it may be placed back onto the main path 170.

FIG. 7 shows a modular approach to the automation system track that can be used for certain embodiments of the present invention. In this example, the tracks may be integrated into individual analyzer stations, such that the track can be used as part of the internal motion or sample handling system of individual lab stations. In the prior art, it is common to have multiple different types of motion systems within different analyzer/testing stations. For example, some stations can include friction tracks for shuttling pucks or trays of sample tubes, and may include carousels containing smaller vessels, such as cuvettes and reaction vessels, into which portions of the sample can be aspirated and dispensed.

In some embodiments, by integrating portions of the track system into the analyzer stations themselves, each station can include its own queuing logic and may be simplified to eliminate unnecessary internal motion systems. Using characterization stations and applying an offset to carriers when positioning at various stations can provide the accuracy and repeatability that may be useful for using an automation track as the primary means for positioning sample vessels within an analyzer module.

With respect to FIG. 7, the track 200 can be broken into modular components that are integrated into analyzer modules. In this exemplary track, modules 205, 205A, and 205B can be combined with one another and optionally other modular track components 202 and 204 to form a track similar to that shown in FIG. 6B. For instance, 205A can be a module that performs the same function as immunoassay 110 (FIG. 5), 205 can be a module that performs the same function as low-volume chemistry module 120 (FIG. 5), and 205B can be a module that performs ISE electrolyte testing, like module 130 (FIG. 5). In this example, the main outer track can be formed by track segments 202, 204, 206, 206A, 206B, 208, 208A, and 208B. Within the analyzer modules 205, 205A, and 205B, internal paths 210, 210A, and 210B form pullouts from the main track. The internal paths can be used for internal queuing and can be managed independently within each analyzer module to allow each module to have greater control over samples to be processed.

One advantage of integrating track 200 and sub-paths 210, 210A, and 210B into the analyzer modules 205, 205A, and 205B, respectively, may be that the internal handling mechanisms within each analyzer module can be specially adapted to better coordinate with the track sub-paths. In some embodiments, modules 205, 205A, and 205B can be adapted to process each sample within a period that is less than an operation cycle of the overall analyzer, leaving enough time for the sample to be routed along the track system to another module after processing, allowing the other module to immediately process the sample on the next operation cycle. As used herein, an operation cycle is a unit of time used by scheduling algorithms to allot processing time to modules for sample assays. These can be dynamic or fixed and can allow synchronous operation of the modules in the analyzer and provide a reliable timing model for scheduling samples amongst multiple modules in the analyzer. The operation cycle time can be chosen to be the time needed by any given module between when it starts processing a first sample, and when it is ready to process another sample under expected steady-state conditions. For example, if an analyzer can process one test every three seconds, and the expected average tests per sample is seven, the operation cycle time can be 21 seconds. It should be understood that individual modules can implement efficiency techniques, such as parallelism or processing multiple samples within a cycle, to maximize throughput, even when the number of tests-per-sample varies from an expected amount. Furthermore, it should be understood that in some embodiments, individual modules have different operation cycle times, and these modules can operate substantially asynchronously from one another. Virtual queues or buffers can be used to assist the management of sample scheduling where cycle times or demand vary between modules.

Enabling transit between modules in the analyzer in a reliable time frame, on the order of a single operation cycle or less, achieves many performance advantages not possible with prior art track systems. If a sample can be reliably handled by an analyzer module and transported to the next analyzer module within a single cycle of the analyzer, traffic handling in queuing becomes much simpler, throughput becomes more consistent, and latency can be controlled and reduced. Essentially, in such an analyzer, a sample can reliably be handled by the track system and processed uniformly such that a sample does not sit idly on the track system waiting in queues. Furthermore, queues within the system, such as queues within a given analyzer module, can reliably be shortened, limited by the number of modules within the system.

In some embodiments of the present invention, the reliable and rapid nature of the track system enables queues to be virtual, rather than physical. A virtual queue can be handled in software, rather than by physical limitations. Traditionally, queues have been physical. The simplest physical queue is effectively a traffic jam at any given part of a sample handling operation. A bottleneck creates a first-in first-out (FIFO) queue, where sample carriers are effectively stopped in a line, providing a buffer so that an analyzer or a decision point can request the next sample in the queue when it is ready. Most prior art lab automation tracks maintain FIFO processing queues to buffer samples that are waiting to be processed by the attached modules (analyzers or pre/post analytic devices). These buffers allow the track to process sample tubes at a constant rate, even though the modules or operator requests can create bursts of demand. FIFO queues can also substantially increase the throughput of the individual modules by allowing them to perform preprocessing tasks for future samples, for example, prepare a cuvette or aspirate reagent, while processing the current sample. While the rigid predictability of FIFO queues enables the parallelization of some processing tasks, it also can prevent the modules from using opportunistic scheduling that may increase throughput by reordering tests on samples to optimize resources. For example, the internal resource conflicts of most immunoassay analyzers can be so complex that the analyzers need to interleave the tests from multiple samples in order to reach maximum efficiency. A FIFO queue can reduce the throughput of these analyzers by as much as 20%. Another challenge with FIFO queues is their inability to handle priority samples (e.g., a STAT sample). If a STAT sample needs to be processed immediately, the entire FIFO queue has to be flushed back onto the main track, delaying all other samples on the track and forcing the original module to slowly rebuild its queue.

Another type of queue is a random access (RA) queue. A carousel is an example of a physical RA queue found in analyzer modules. By aliquoting a portion of a sample into one or more vessels in a carousel ring, an analyzer module can select any of a number of samples to process at any time within the analyzer. However, carousels may have drawbacks, including added complexity, size, and cost. A carousel also increases the steady-state processing time, because a sample must be transferred into and out of the random-access queue. Processing delays depend on the implementation, such as the number of positions in a carousel. On the other hand, by having random access to samples, a local scheduling mechanism within a module can process samples in parallel, performing sub-steps in any order it desires.

In some embodiments, carousels or other physical RA queues can be eliminated from the modules and the sub-paths (e.g., 210) from the automation system can be used as part of an RA or FIFO queue. That is, if the travel time for a sample between any two points can be bounded to a known time that is similar to that of a carousel, (such as predictably less than a portion of an operation cycle), the track 200 can be part of the queue for a given module. For example, rather than using a carousel, module 205 can utilize samples in carriers on sub-path 210. Preprocessing steps, such as reagent preparation, can be conducted prior to the arrival of a sample under test. Once that sample under test arrives, one or more portions of the sample can be aspirated into cuvettes or other reaction vessels for an assay. In some embodiments, these reaction vessels can be contained within module 205, off track, while in other embodiments, these reaction vessels can be placed in carriers on sub-path 210 to allow easy motion. If the sample under test is required to be at a module for longer than an operation cycle, or if multiple samples will be processed by the module during an operation cycle, the sub-path 210 can act as a queue for the module.

Furthermore, samples not yet under test, which may be currently located at other modules, can be scheduled for the next operation cycle. These next-cycle samples can be considered as residing in a virtual queue for module 205. A module can schedule samples to arrive during a given operation cycle for any sample on track 200. A central controller, or controllers associated with modules themselves, can resolve any conflicts over a sample for a given cycle. By giving a module prior knowledge of the arrival time of a sample, each module can prepare resources and interleave tests or portions of tests to more efficiently allot internal resources. In this manner, modules can operate on samples in a just-in-time manner, rather than by using large physical buffers. The effect is that the virtual queue for a given module can be much larger than the physical capacity of the sub-path serving that module, and existing scheduling algorithms can be used. Effectively, each module can treat track 200 as it would treat a sample carousel in a prior art module.

It should be appreciated that by employing virtual queues, in some embodiments, multiple modules can have multiple queues and can share a single queue or samples within a queue. For example, if two modules are equipped to perform a certain assay, a sample needing that assay can be assigned to a virtual queue for that assay, which is shared between the two modules capable of handling the assay. This allows load balancing between modules and can facilitate parallelism. In embodiments where reaction vessels are placed in carriers on track 200, an assay can be started at one module (e.g., reagents prepared and/or sample mixed in) and the assay can be completed at another (e.g., a reaction is observed at another module). Multiple modules can effectively be thought of as a multi-core processor for handling samples in some embodiments. In these embodiments, scheduling algorithms for the multiple modules should be coordinated to avoid conflicts for samples during a given operation cycle.

By employing virtual queues, modules can operate on samples while the samples are in the virtual queues of other modules. This allows low latency of samples, as each sample that is placed onto track 200 can be processed as quickly as the modules can complete the tests, without having to wait through a physical queue. This can greatly reduce the number of sample carriers on track 200 at any given time, allowing reliable throughput. By allowing modules to share queues or samples, load balancing can also be used to maximize throughput of the system.

Another advantage of using virtual queues is that STAT samples can be dynamically assigned priority. For example, a STAT sample can be moved to the head of any queue for the next operation cycle in software, rather than having to use a physical bypass to leapfrog a STAT sample to the head of a largely static physical queue. For example, if a module is expecting three samples to be delivered by track 200 for assays during the next operation cycle, a scheduler responsible for assigning samples to the module can simply replace one or more of the samples with the STAT sample, and have the track 200 deliver the STAT sample for processing during the next operation cycle.

If decision points, such as decision points 214 and 216, can be streamlined such that there is no need for a queue at each decision point, the only physical queues can be within sub-paths 210, 210A, and 210B. As described above, these can be treated as RA queues or FIFO queues. If a STAT sample is placed onto track 200, RA queues within sub-paths 210, 210A, and 210B need not be flushed, as the STAT sample can be processed immediately. Any FIFO queues can be individually flushed. For example, if a STAT sample is placed onto track 200 at section 222, the sample may be routed to the appropriate analyzer 205B via the outside track and decision point 216. If there are other samples (and by extension the sample carriers transporting those samples) waiting in the queue in path 210B, only those samples in the queue may need to be flushed to allow a STAT sample to take priority. If the outer track 200 is presumed to take less than an operation cycle to traverse, any samples that were flushed from the queue in 210B can simply be circulated around the track and placed immediately back into the queue in path 210B immediately behind the STAT sample, eliminating any down time caused by the STAT sample.

Entry paths 220 and 222 can be used to input samples to the track 200. For example, regular priority samples can be placed onto track 200 at input 220 and STAT priority samples can be placed on input 222. These inputs can be used as outputs for samples when complete, or other ports (not shown) can be used as the output paths for used samples. Input 220 can be implemented as an input buffer, acting as a FIFO queue for input samples seeking access to the track 200. Once a sample reaches the head of the queue at input 220, it can be moved onto the track (either by being placed in a carrier or by being placed in a carrier when it is placed in input 220). A STAT sample can enter the track 200 immediately after being placed at input 222 or, if track 200 is overcrowded, the STAT sample can enter the track at the next available uncrowded operation cycle. Some embodiments monitor the number of carriers on the track during an operation cycle and limit the total number to a manageable amount, leaving the remainder in input queues. By restricting samples at the input, track 200 can be free of traffic, allowing it to always be operated in the most efficient manner possible. In these embodiments, the transit time of a sample between two modules can be a bounded value (e.g., less than some portion of an operation cycle), allowing simplified scheduling.

In some embodiments, the track system 200 can be designed to be bidirectional. This means that sample carriers can traverse the outside path and/or any sub-paths in either direction. In some embodiments, additional sub-paths, such as 211B accessed via additional decision points 215 and 217, can assist in providing bidirectional access. Bidirectional paths can have inherent advantages. For example, if normal priority samples are always handled in the same direction, a STAT sample can be handled in the opposite direction along the sub-path. This means that a STAT sample can essentially enter the exit of the sub-path and be immediately placed at the head of the queue without requiring the queue to be flushed. For example, if a STAT sample is placed on track 200 at segment 204, it can enter path 210B via decision point 214 and proceed into path 210B to be immediately placed at the head of any queue. Meanwhile, in all of these examples, because queues are presumed to be limited generally to sub-paths, there is no need to flush queues in other modules if a STAT sample does not need immediate access to those modules. Any additional modules that need to service a STAT sample on a subsequent cycle can flush their queues at that point, providing "just-in-time" access to a STAT sample without otherwise disrupting the operation of each analyzer module.

Modular design also allows certain other advantages. If the automation systems within an analyzer module are adapted to take advantage of the track system contained in the module, new features can be added that use the common track. For example, a module could have its own internal reagent carousel that includes all of the reagents necessary for performing the assays prescribed for the samples. When reagents stocked in the analyzer module run low, an operator can replenish the reagents in some embodiments by simply loading additional reagents onto carriers on the track 200. When the reagents on track 200 reach the appropriate module, the module can utilize mechanical systems such as an arm or a feeder system that takes the reagents off of the track and places the reagents in the reagents store for the module.

In some embodiments, the individual track portions shown in FIG. 7 and FIG. 6A and FIG. 6B can be operated independently from one another, or can be passive. Independent carrier movement can provide advantages over friction-based track systems (such as non-localized conveyor belts where the entire friction track must be moved to effect movement of a sample carrier). This means that other samples also on that track must move at the same rate. This also means that if certain sections operate at different speeds, collisions between passive carriers carrying samples can occur.

FIG. 8A depicts an exemplary carrier 250 for use with some embodiments of the present invention. Carrier 250 can hold different payloads in different embodiments. One payload can be a sample tube 255, which contains a fluid sample 256, such as blood or urine. Other payloads may include racks of tubes or reagent cartridges or any other suitable cartridge. Sample carrier 250 includes a main body 260, which can house the internal electronic components describe herein. The main body 260 supports a bracket 262, which can accept a payload. In some embodiments, this is a shallow hole that is designed to accept a fluid container 255 such as a sample tube, and hold it with a friction fit. In some embodiments, the friction fit can be made using an elastic bore or a clamp that can be fixed or energized with a spring to create a holding force. In some embodiments, sample racks and reagent cartridges can be designed to also attach to the bracket 262, allowing bracket 262 to act as a universal base for multiple payload types.

Body 260 can include or be coupled to guide portion 266, which allows the carrier 250 to follow a track between decision points. Guide portion 266 can include, for example, a slot to accept one or more rails in the track, providing lateral and/or vertical support. In some embodiments, the guide portion allows the carrier 250 to be guided by walls in the track, such as the walls of a trough shaped track. The guide portion 266 can also include drive mechanisms, such as friction wheels that allow a motor in the carrier body 260 to drive the carrier or puck 250 forward or backward on the track. The guide portion 266 can include other drive components suitable for use with the embodiments described throughout, such as magnets or induction coils.

Rewritable display 268 can be provided on the top of the carrier 250. This display can include an LCD oriented panel and can be updated in real time by the carrier 250 to display status information about sample 256. By providing the electronically rewritable display 268 on the top of the carrier 250, the status information can be viewed at a glance by an operator. This can allow an operator to quickly determine which sample he/she is looking for when there are multiple carriers 250 in a group. By placing the rewritable display 268 on top of the carrier 250, an operator can determine status information even when multiple carriers 250 are in a drawer or rack.

FIG. 8B shows an exemplary track configuration 270 for use by carriers 250. In this example, carriers 250A transport sample tubes, while carriers 250B transport racks of tubes along main track 272 and/or subpaths 274 and 274A. Path 276 can be used by an operator to place samples into carriers or remove samples from these carriers.

Figure 8C:
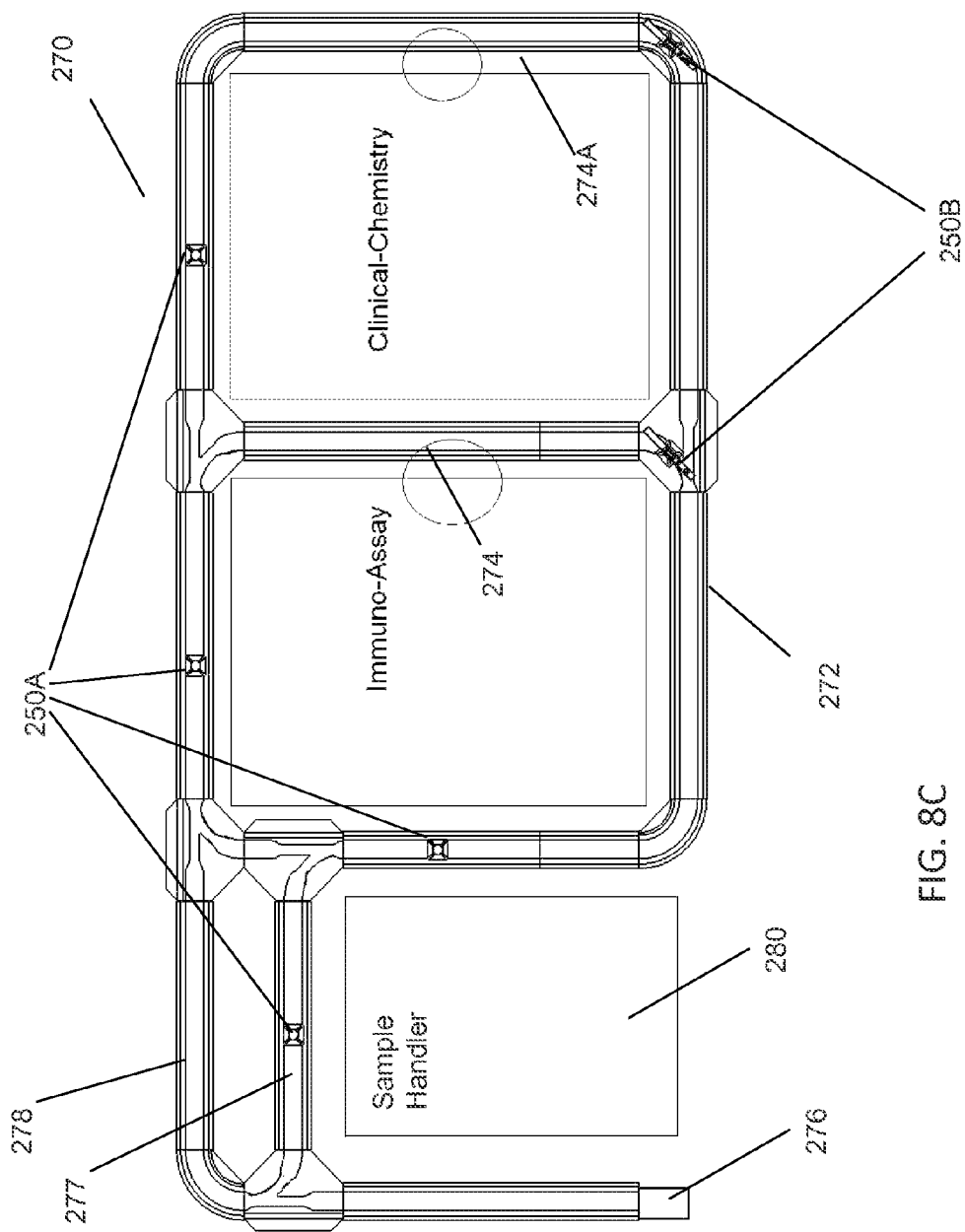
FIG. 8C is a top view of an exemplary automation system that can be used with the embodiments disclosed herein.

FIG. 8C shows an additional view of an exemplary track configuration 270. In this example, sub-path 274 serves an immunoassay station, while subpath 274A serves a clinical chemistry station. Input/output lane 276 can be served by a sample handler station 280 that uses sub paths 277 and 278 to buffer samples for insertion or removal of the samples from the main track 272.

In some embodiments, the sample handler 280 can also load and unload samples or other payloads to/from the carriers 250A and 250B. This allows the number of carriers to be reduced to the amount needed to support payloads that are currently being used by the stations in track system 270, rather than having a vast majority of carriers sitting idle on tracks 277 and 278 during peak demand for the analyzer. Instead, sample trays (without the carriers disclosed herein) can be placed/removed by an operator at input/output lane 276. This can reduce the overall cost of the system and the number of carriers needed can be determined by the throughput of the analyzer, rather than based on anticipating the peak demand for the analyzer in excess of throughput.

Intelligent Carriers

In some embodiments, intelligent carriers can enable certain improvements over passive pucks on the friction-based tracks. For example, one disadvantage of prior art track systems is that at each decision point the decision for directing a puck is made by the track by rotating the puck and reading a barcode optically. Rotating and optical reading is a relatively slow process. Furthermore, this process can be redundant because the system has knowledge of the identification of the sample tube when the sample tube is placed into the puck by an operator. Embodiments of the present invention can include carriers that have means to identify the contents of the sample tube (and optionally communicate this information to the automation system) without requiring the carrier to be stopped, rotated, and read optically.

For example, a carrier can include an onboard optical reader to automatically read a barcode of a payload. The results of the scan can then be stored in the memory of a carrier if the carrier has onboard processing capability. Alternatively, an outside source, such as a processor coupled to a hand barcode reader operated by an operator at the time of placing the sample into the carrier, can communicate the barcode information of the payload to the carrier via RF signal or other known means, such as communication protocol using temporary electrical contact or optical communication. In some embodiments, the association of the carrier with the payload can be stored external to the carrier and the identity of the carrier can be conveyed by the carrier to the system by RF, optical, or near-field communication, allowing the system to assist in routing or tracking the carrier and the payload. Routing decisions can then be made by the carrier or by identifying the carrier, rather than reading a unique barcode of a payload.

By moving processing capability and/or sensor capability onto each individual carrier, the carriers can participate actively and intelligently in their own routing through the track system. For example, if individual carriers can move independently of one another either by autonomous motive capabilities or by communication with the track, certain performance advantages can be realized.

In some embodiments, by allowing carriers to move independently, carriers can move around the track faster. One key limitation on the motion of a carrier is that it should not spill an open-tube sample. The limiting factor is generally not the velocity of the carrier in a straight line, but the acceleration and jerk experienced by the carrier (while speeding up, slowing down, or turning), which may cause splashing. For friction-based track systems, the velocity of the track is typically limited to prevent acceleration and jerk experienced by pucks from exceeding threshold amounts because the entire track moves. However, by using a track system with independently operating sections that can respond to individual carriers, or individual carriers that have independent motive capability, the acceleration of any given carrier can be tailored to limit acceleration/deceleration and jerk, while allowing the average velocity to be greater than that of traditional tracks. By not limiting the top speed of a carrier, the carrier can continue to accelerate on each track section as appropriate, resulting in a substantially higher average speed around the track. This can assist the carrier in traversing the entire track system in less than one machine cycle of the analyzer. These machine cycles can be, for instance, 20 or 40 seconds.

Similarly, in some embodiments, an autonomous carrier can know its own identity and that of its payload. This allows the carrier to actively participate or assist in the routing decision process at individual decision points. For example, upon reaching a decision point (e.g., switch, intersection, junction, fork, etc.), a carrier can communicate its identity and/or the identity of its payload to the track or any switching mechanism (or its intended route that the carrier has determined based on the payload identity), via RF or near-field communication. In this scenario, the carrier does not need to be stopped at a decision point for a barcode scan. Instead, the carrier can keep going, possibly without even slowing down, and the carrier can be routed in real time. Furthermore, if the carrier knows where it is going or communicates its identity to the track (such that the track knows where the carrier is going) before the carrier physically reaches a decision point, the carrier can be made to decelerate prior to a decision point if the carrier will be turning. On the other hand, if the carrier does not need to turn at the decision point, the carrier can continue at a higher velocity because the sample carried by the carrier will not undergo cornering forces if the carrier is not turning at the decision point or a curved section of the track.

In some embodiments, an autonomous carrier can also include onboard processing and sensor capabilities. This can allow a carrier to determine where it is on the track and where it needs to go, rather than being directed by the track (although in some embodiments, a central controller sends routing instructions to the carrier to be carried out). For example, position encoding or markers in the track can be read by a carrier to determine the carrier's location. Absolute position information can be encoded on a track surface to provide reference points to a carrier as it traverses the track. This position encoding can take many forms. The track may be encoded with optical markers that indicate the current section of the track (e.g., like virtual highway signs), or may further include optical encoding of the specific absolute location within that section of track (e.g., like virtual mile markers). Position information can also be encoded with markings between absolute position marks. These can provide synchronization information to assist a carrier in reckoning its current trajectory. The optical encoding scheme may take on any appropriate form known to one skilled in the art. These marks used by the encoding scheme may include binary position encoding, like that found in a rotary encoder, optical landmarks, such as LEDs placed in the track at certain positions, barcodes, QR codes, data matrices, reflective landmarks, or the like. General position information can also be conveyed to the carrier via RF/wireless means. For example, RFID markers in the track can provide near field communication to the carrier to alert the carrier that it has entered a given part of the track. In some embodiments, local transmitters around or near the track can provide GPS-like positioning information to enable the carrier to determine its location. Alternatively, sensors in the track, such as Hall effect sensors or cameras, can determine the position of individual carriers and relay this information to the carrier.

Similarly, the carrier can have sensors that indicate relative motion, which provide data that can be accumulated to determine a position. For example, the carrier may have gyroscopes, accelerometers, or optical sensors that observe speckle patterns as the carrier moves to determine velocity or acceleration, which can be used to extrapolate a relative position.

Because a carrier can know where it is and its motion relative to the track, a carrier can essentially drive itself, provided it knows its destination. The routing of the carrier can be provided in many different ways in various embodiments. In some embodiments, when a carrier is loaded with the sample, the system can tell the carrier the destination analyzer station. This information can be as simple as the identification of the destination station in embodiments where the carrier has autonomous routing capability. This information can also be detailed information such as a routing list that identifies the specific path of the individual track sections and decision points that a carrier will traverse. Routing information can be conveyed to the carrier via any communication method described herein, such as RF communication, near field/inductive communication, electrical contact communication, or optical communication.

In an exemplary embodiment, when an operator scans the barcode of the sample tube and places it in a carrier, the system determines the identity of the carrier and matches it with the identity of the sample. The system then locates the record for the sample to determine which tests the sample must undergo in the analyzer. A scheduler then allocates testing resources to the sample, including choosing which tests will be done by individual testing stations and when the sample should arrive at each testing station for analysis. The system can then communicate this schedule (or part of the schedule) to the carrier to inform the carrier of where it needs to go, and optionally when it needs to go and/or when it needs to arrive.

Once the carrier is placed onto the track system, the routing capabilities and location acquisition systems of the carrier enable the carrier to determine where it is on the track and where it needs to go on the track. As the carrier traverses the track, the carrier reaches individual decision points and can be directed along the main track or along sub-paths as appropriate. Because each carrier operates independently from one another, a carrier can do this quite quickly without necessarily stopping at each decision point and without waiting for other carriers in a queue. Because these carriers can move quickly, there may be less traffic on the main sections of the track, which reduces the risk of collision or traffic jams at decision points or corners in the track (e.g., sections where carriers might slow down to avoid excessive forces on the sample).

Motive force can be provided to the carriers in many ways. In some embodiments, the track actively participates in providing individualized motive force to each carrier. In some embodiments, motive force is provided by electromagnetic coils in the track that propel one or more magnets in the carrier. An exemplary system for providing this motive force is the track system provided by MagneMotion, Inc., which can generally be understood by the description of the linear synchronous motors (LSMs) found in US Published Patent Application 2010/0236445, assigned to MagneMotion, Inc. These traditional systems utilizing this magnetic motion system have included passive carriers that lack the integrated intelligence of the carriers described herein, and all routing and decisions are made by a central controller with no need for active carriers that participate in the routing and identification process.

In embodiments that utilize magnetic motion, the electromagnetic coils and the magnets operate as an LSM to propel each individual carrier in the direction chosen with precise control of velocity, acceleration, and jerk. Where each coil on the track (or a local set of coils) can be operated independently, this allows highly localized motive force to individual carriers such that individual carriers can move with their own individually tailored accelerations and velocities. Coils local to a carrier at any given moment can be activated to provide precise control of the direction, velocity, acceleration, and jerk of an individual carrier that passes in the vicinity of the coils.

In some embodiments, a track may be comprised of many individually articulable rollers that act as a locally customizable friction track. Because individual micro-sections of the track can be managed independently, rollers immediately around a carrier may be controlled to provide individualized velocity, acceleration, and jerk. In some embodiments, other active track configurations can be used that provide localized individual motive force to each carrier. In some embodiments, tracks move with more precision near instruments.

In some embodiments, the track may be largely passive, providing a floor, walls, rails, or any other appropriate limitations on the motion of a carrier to guide the carrier along a single dimension. In these embodiments, the motive force is provided by the carrier itself. In some embodiments, each individual carrier has one or more onboard motors that drive wheels to provide self-propelled friction-based motive force between the track and the carrier. Unlike traditional friction tracks, where the track is a conveyor, carriers with driven wheels can traverse the track independently and accelerate/decelerate individually. This allows each carrier to control its velocity, acceleration, and jerk at any given moment to control the forces exerted on its payload, as well as traverse the track along individually tailored routes. In some embodiments, permanent magnets may be provided in the track and electromagnets in the carrier may be operated to propel the carrier forward, thereby acting as an LSM with the carrier providing the driving magnetic force. Other passive track configurations are also contemplated, such as a fluid track that allows carriers to float and move autonomously via water jets or the like, a low friction track that allows carriers to float on pockets of air provided by the track, (e.g., acting like a localized air hockey table), or any other configuration that allows individual carriers to experience individualized motive forces as they traverse the track.

Figure 9:
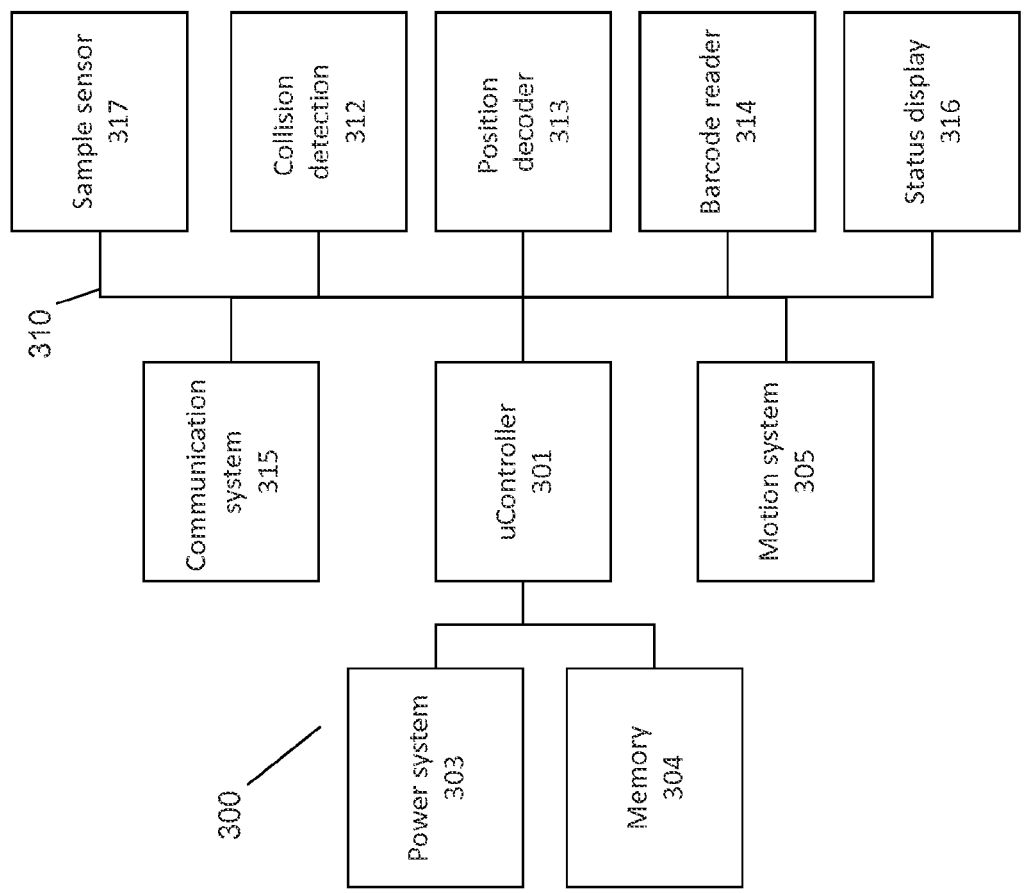
FIG. 9 is a system block diagram of the control systems including onboard active carriers that can be used with certain embodiments disclosed herein.

FIG. 9 shows a top level system diagram of the control systems and sensors for an exemplary intelligent autonomous carrier 300. Carrier 300 is controlled by a microcontroller 301 that includes sufficient processing power to handle navigation, maintenance, motion, and sensor activities needed to operate the carrier. Because the carrier is active and includes onboard electronics, unlike prior art passive carriers, the carrier includes an onboard power station. The details of this station vary in different embodiments of the present invention. In some embodiments, power system 303 comprises a battery that may be charged as the carrier operates, while in other embodiments, the battery is replaceable or can be manually charged when the carrier is not operating. Power system 303 can include the necessary charging electronics to maintain a battery. In other embodiments, power system 303 comprises a capacitor that may be charged by inductive or electrical contact mechanisms to obtain electrical potential from the track itself, in much the same way a subway car or model train might receive power.

Microcontroller 301 communicates with system memory 304. System memory 304 may include data and instruction memory. Instruction memory in memory 304 includes sufficient programs, applications, or instructions to operate the carrier. This may include navigation procedures as well as sensor handling applications. Data memory in memory 304 can include data about the current position, speed, acceleration, payload contents, navigational plan, identity of the carrier or payload, or other status information. By including onboard memory in carrier 300, the carrier can keep track of its current status and uses information to intelligently route around the track or convey status information to the track or other carriers.

Microcontroller 301 is responsible for operating the motion system 305, sensors 312, 313, and 314, communication system 315, status display 315, and sample sensor 317. These peripherals can be operated by the microcontroller 301 via a bus 310. Bus 310 can be any standard bus, such as a CAN bus, that is capable of communicating with the plurality of peripherals, or can include individual signal paths to individual peripherals. Peripherals can utilize their own power sources or the common power system 303.

Motion system 305 can include the control logic necessary for operating any of the motion systems described herein. For example, motion system 305 can include motor controllers in embodiments that use driven wheels. In other embodiments, motion system 305 can include the necessary logic to communicate with any active track systems necessary to provide a motive force to the carrier 300. In these embodiments, motion system 305 may be a software component executed by microcontroller 301 and utilizing communication system 315 to communicate with the track. Devices such as motors, actuators, electromagnets, and the like, that are controlled by motion system 305 can be powered by power system 303 in embodiments where these devices are onboard the carrier. External power sources can also provide power in some embodiments, such as embodiments where an LSM provides motive force by energizing coils in the track. In some embodiments, motion system 305 controls devices on or off the carrier to provide motive force. In some embodiments, the motion system 305 works with other controllers, such as controllers in the track, to coordinate motive forces, such as by requesting nearby coils in the track be energized or requesting the movement of local rollers. In these embodiments, motion system 315 can work together with communication system 315 to move the carrier.

Carrier 300 can include one or more sensors. In some embodiments, carrier 300 includes a collision detection system 312. Collision detection system 312 can include sensors at the front or back of a carrier for determining if it is getting close to another carrier. Exemplary collision detection sensors can include IR range-finding, magnetic sensors, microwave sensors, or optical detectors. Whereas many prior art pucks are round, carrier 300 may be directional, having a front portion and a rear portion. By having a directional geometry, carrier 300 can include a front collision detector and a rear collision detector.

In some embodiments, collision detection information can include information received via the communication system 315. For example, in some embodiments, the central controller for the track can observe the location and speed of carriers on the track and evaluate collision conditions and send updated directions to a carrier to prevent a collision. In some embodiments, nearby carriers can communicate their positions in a peer-to-peer manner. This allows carriers to individually assess the risk of collision based on real-time position information received from other carriers. It will be understood that in embodiments where the carrier receives trajectory information about other carriers, or decisions are made with the help of a centralized controller that has access to trajectory information of nearby carriers, the carriers need not be directional, and can include sensors or receivers that do not depend on a given orientation of a carrier.

Carrier 300 can also include a position decoder 313. This sensor can extrapolate the carrier's position as described herein. For example, position decoder 313 can include a camera or other optical means to identify landmarks in the track, or observe optical encoding in the track. In some embodiments, position decoder 313 can also include inertial sensors, magnetic sensors, or other sensors sufficient to determine a carrier's current position, direction, velocity, acceleration, and/or jerk.

Carrier 300 can optionally include a barcode reader 314. If equipped with the barcode reader 314, carrier 300 can observe the barcode of its payload at the time the samples are loaded onto the carrier or at any time thereafter. This prevents the need for a carrier to stop at individual decision points to have the system read the barcode of a sample tube. By reading and storing the identity of the sample tube, or conveying this information to the overall system, a carrier may more efficiently traverse the track system because routing decisions can be made in advance of reaching a decision point. Alternatively, where a system knows the identity of the sample when it is placed onto the carrier, the system can include an external barcode reader and can convey the identity of the payload to the carrier for storage and memory 304 via communication system 315.

Communication system 315 can comprise any mechanisms sufficient to allow the carrier to communicate with the overall automation system. For example, this can include an XBee communication system for wireless communication using an off-the-shelf communication protocol, such as 802.15.4, any appropriate version of 802.11, or any standard or proprietary wireless protocol. Communication system 315 can include a transceiver and antenna and logic for operating an RF communication protocol. In some embodiments, communication system 315 can also include near-field communication, optical communication or electrical contact components. Information conveyed via the communications system to/from carrier 300 is described throughout this application.

In some embodiments, the carrier can also include a status display module 316. The status display module 316 can include a controller and rewritable electronic display, such as an LCD panel or E-ink display. In some embodiments, the controller is treated as an addressable portion of memory, such that the microcontroller 301 can easily update the status display 316.

In some embodiments, the carrier also includes sample sensor 317. This sensor can be used to indicate the presence or absence of a fluid container in the carrier's tube bracket (which may also be referred to as a tube holder). In some embodiments, this is a momentary mechanical switch that is depressed by the presence of a tube and not depressed when a tube is absent. This information can be used to determine the status of a tube, which can assist in the display of status information by status display module 316.

Routing

In some embodiments, substantially instantaneous trajectory observation and control is conducted on board each carrier to facilitate real-time control, while the overall routing decisions are made by a central controller that manages a group of carriers. Therefore, in some embodiments of the present invention, the carriers act like semi-autonomous robots that receive global routing instructions from a central controller, but make local motion decisions substantially autonomously.

For example, when a carrier receives a sample (e.g., a patient fluid sample or other payload) a central controller managing one or more carriers determines the schedule for that carrier and instructs the carrier where to go on the track of, for example, an in vitro diagnostics automation system. This instruction can be a next-hop instruction (e.g., identifying the next leg of a route), such as going to a given decision point, moving forward to the next decision point, or turning at a given decision point. In some embodiments, the instructions can include a complete or partial list of track segments and decision points to be traversed and whether to turn at each decision point. These instructions can be communicated to the carrier from a central controller via any conventional means, including wireless or contact electrical signaling, as explained throughout this disclosure.

While following the instructions, each carrier can make a determination of the appropriate velocity, acceleration, and jerk (as used herein, acceleration includes deceleration). This can include a real-time decision of whether the carrier must slow down to avoid collision or to enter a curve without causing excessive lateral forces, or slow down before the next decision point. These decisions can be made with the assistance of any onboard sensors, as well as external information received by the carrier, such as information about the position and trajectory of nearby carriers. For example, accelerometers and/or track encoding information can be used to determine the current velocity, acceleration, and jerk, as well as the current position of a carrier. This information can be used by each carrier to determine its trajectory and/or can be conveyed to other carriers. Collision detectors, such as RF rangefinders, can determine whether or not a potential collision condition exists to assist the carrier in determining whether it needs to slow down and/or stop. This collision determination can include trajectory information about the current carrier, as well as the trajectory information about surrounding carriers received by the current carrier through observation or by receiving information from a central scheduler for the track.

Figure 10:
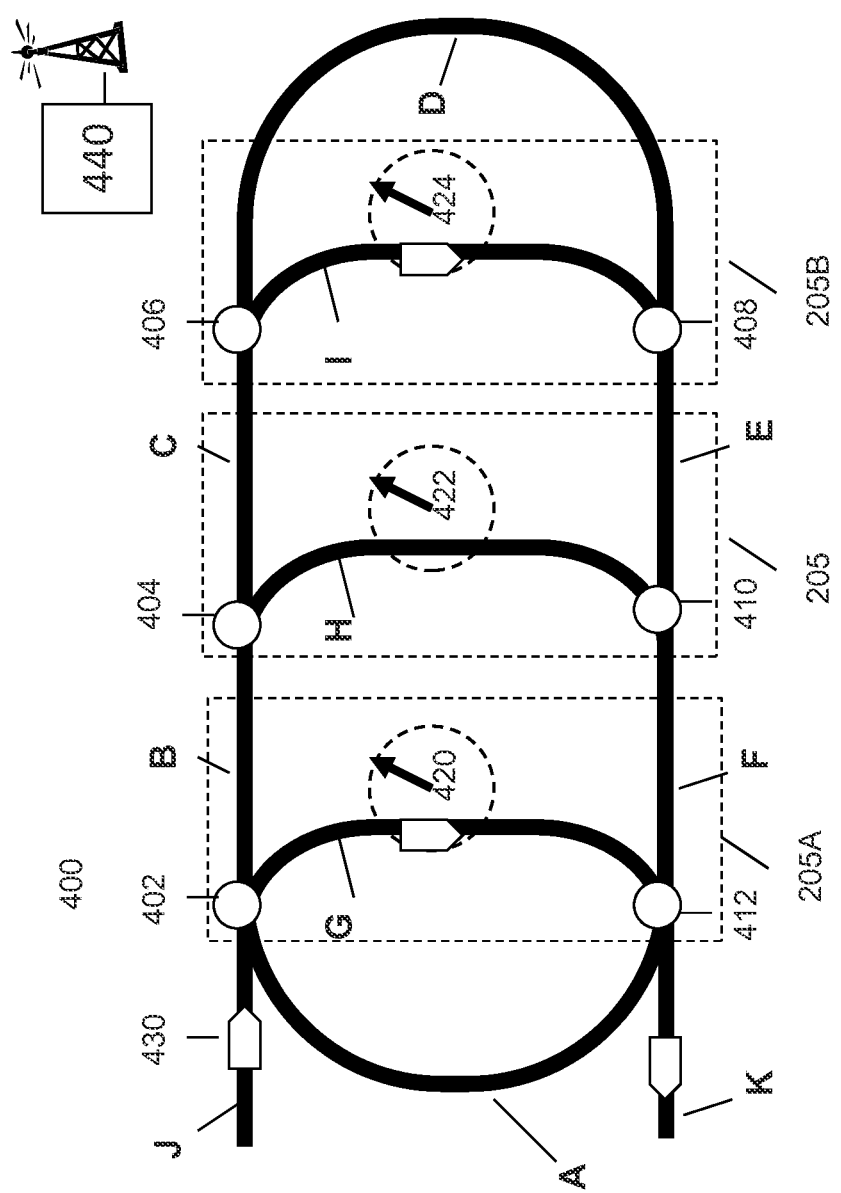
FIG. 10 is a diagrammatic view of exemplary routes in an exemplary track configuration that can be used for navigation of sample carriers in certain embodiments.

FIG. 10 shows an exemplary routing scenario in automation system 400. Carrier 430 receives routing instructions from central management processor 440 via RF signaling. Central management processor 440 can participate in monitoring and directing carriers, including issuing routing instructions and scheduling the movement and dispatch of carriers. Central management processor 440 can be part of the central controller and/or local controllers that interact with individual modules or stations. Central or local controllers can also act at the direction of central management processor 440. Central management processor 440 can include one or more processors operating together, independently, and/or in communication with one another. Central management processor 440 can be a microprocessor, software operating on one or more processors, or other conventional computer means suitable for calculating the schedule for multiple carriers within the track system 400.

Central management processor 440 can receive position information from multiple carriers, as well as any sensor information from sensors in the track system 400 and/or information reported by the carriers. Central management processor 440 uses the status information of the carriers and track as well as the identity of samples or other payload carried by the carriers and the required assays to be performed by the system on these samples.

The exemplary track 400 shown in FIG. 10 includes a first curve segment A, that connects to straight segment B and a pullout segment G (e.g., a segment that serves a testing station), which serves analyzer/testing station 205A and pipette 420, via decision point 402. Segment B connects to straight segment C and a pullout segment H, which serves analyzer/testing station 205 and pipette 422, via decision point 404. Segment C connects to curved segment D, which serves sample handling station 205C, and pullout segment I, which serves analyzer/testing station 205B and pipette 424, via decision point 406. Segment D connects to straight segment E and the other end of pullout segment I, via decision point 408. That is, there are different paths between decision points 406 and 408—segments D and I (where segment I is a pullout that can be used to deliver samples to interact with pipette 424). Segment E connects to straight segment F and the other end of pullout segment H, via decision point 410. Segment F connects to curved segment A and the other end of pullout segment G, via decision point 412. In some embodiments, track 400 includes input and output lanes J and K, which can be used to add or remove carriers at decision points 402 and 412.

In some embodiments, decision points 402-412 are passive forks in the track that carrier 430 can navigate to select a proper destination segment. In other embodiments, decision points 402-412 are active forks that can be controlled by carrier 430 or central management processor 440. In some embodiments, decision points 402-412 are electromagnetically controlled switches that respond to requests by carrier 430, such as via RF or near field communication. In some embodiments these electromagnetically controlled switches have a default position, such as straight, that the switch will return to once a carrier has been routed. By using default positions for decision points, a carrier may not need to request a position at each decision point, unless it needs to be switched at that decision point.

Scheduler central management processor 440 assigns carrier 430 a first route, Route 1, to place the carrier 430 and its payload within reach of pipette 420. Carrier 430 is instructed to travel along segment J to decision point 402 and travel onto segment G to stop at a position accessible to pipette 420. In some embodiments, carrier 430 receives the instructions and determines its current location and trajectory to determine a direction and trajectory to use to reach decision point 402. Carrier 430 can also take into account that it will be making a hard right turn at decision point 402 onto segment G. In some embodiments, decision point 402 includes a switching mechanism in the track that can operate under the control of carrier 430. In these embodiments, carrier 430 communicates with the track on approach to decision point 402 to request switching onto segment G. In other embodiments, carrier 430 may have a steering mechanism (such as moveable guide wheel, directional magnets, asymmetric brakes, or the like) that allows carrier 430 to make a right turn onto segment G at decision point 402, without the assistance of an external gate integrated into the track. In these embodiments, carrier 430 engages the steering mechanism at decision point 402 to make the turn onto segment G.

Carrier 430 can determine its rough location—its current track section, such as section J, by reading encoding in the track, such as optical encoding, or RFID tags. In some embodiments, carrier 430 uses multiple means to determine its location within the track system 400. For example, RFID tags can be used to determine generally on which track segment the carrier 430 is located, while optical encoding or other precise encoding can be used to determine the position within that track segment. This encoding can also be used to determine velocity, acceleration, or jerk by observing changes in the encoding (e.g., derivatives from the position information).

Carrier 430 can use the identification of the current track section to determine the appropriate route to the destination section either by explicit instruction received by the central management processor 440 or by looking up an appropriate route in an onboard database in memory 304, as shown in the onboard control systems in FIG. 5. In some embodiments, the carrier 430 has an understanding of how to reach section G from section J based on a map stored in the memory of carrier 430 in memory 304. This map can include a simple lookup table or a tree of track sections where each node is linked by the corresponding decision points, or vice versa. For example, upon identifying that the carrier is currently in the track section J, the onboard database can inform carrier 430 to proceed to decision point 402 to be switched to the right onto section G.

Central management processor 440 can instruct carriers to stop at positions to interact with pipette 420, 422, or 424. By utilizing a characterization station to characterize offsets between the position of sample tubes carried by a carrier and some known position on the carrier, such as the location on a carrier that would ordinarily come to rest at a fixed stopping position to interact with each of these pipettes, central management processor 440 can instruct carriers or local track resources interacting with the carriers to stop the carrier at a position that compensates for any measured offset. This can allow pipettes 420, 422, or 424 to repeatably interact with sample tubes at fixed locations on the respective track sections, even though carriers transporting the sample tubes may come to rest at locations that vary from carrier to carrier and tube to tube.

In some embodiments, carriers can utilize local track encoding around the pipettes to assist in accurately placing the carrier at a stopping position that compensates for measured offsets. Encoding can include optical marks or the like and localized encoding may assist in positioning the carrier at a desired position that is incrementally spaced from an optical mark. In some embodiments, magnetic positioning may be used whereby Hall effect sensors can accurately measure the current location of the carrier and electromagnets can be used to maneuver carrier to a final resting position with fine precision. In some embodiments, the incremental distances that may be used to position a carrier relative to a fixed stopping point may be less than 1 mm. Suitable encoding schemes that may be used for encoding position information, as well as offsets from known positions, may include those encoding schemes described in PCT Patent Application PCT/US13/42022, filed May 21, 2013, which is incorporated by reference herein in its entirety.

In some embodiments, local track sections behave differently from main track sections, allowing finer precision when placing carriers at locations to interact with instruments. For example, main track section may be capable of positioning a carrier with large resolution, such as several inches, whereas a local track section may include finer precision components that allow a carrier to be positioned within fractions of the millimeter.

Figure 11:
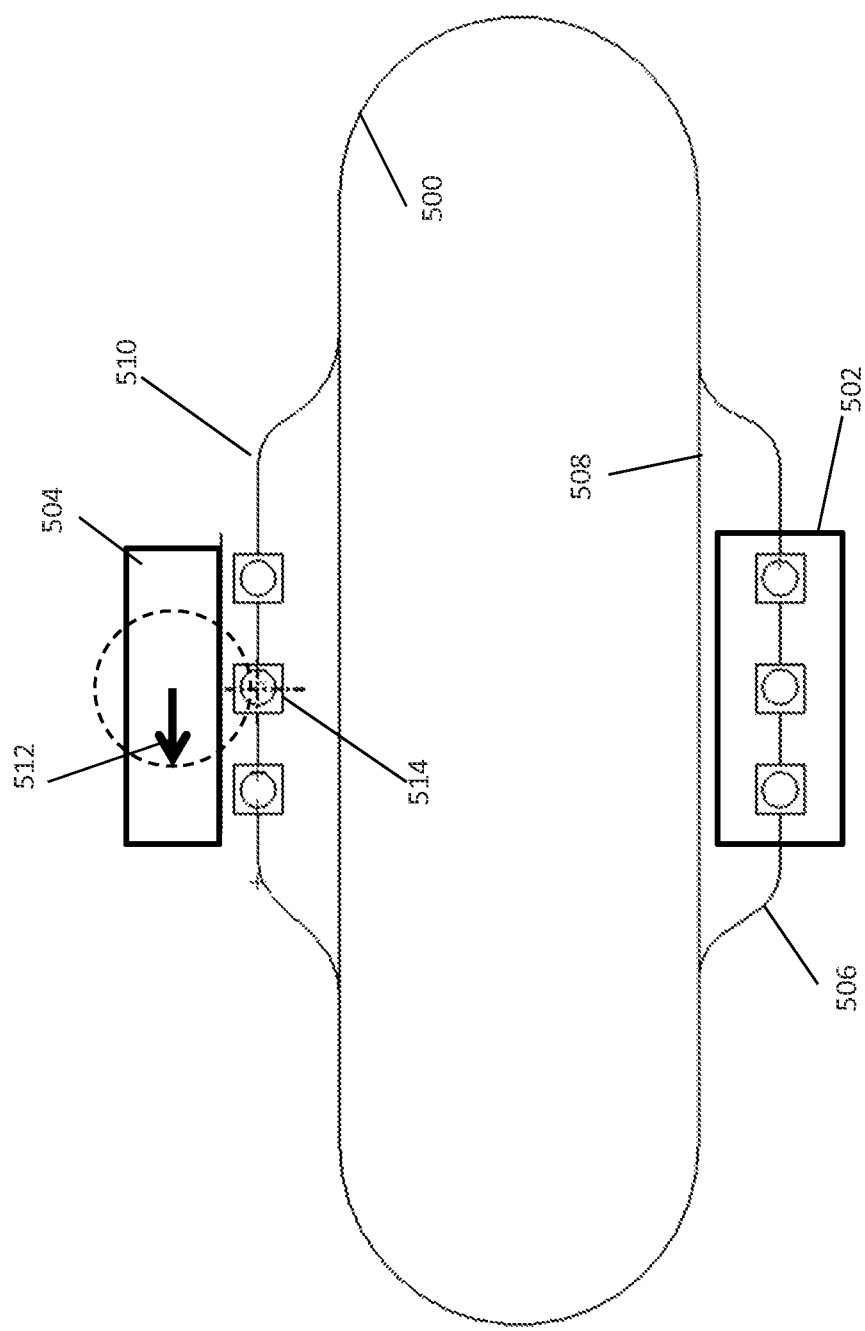
FIG. 11 is a top view of an exemplary automation track for use with some embodiments.

FIG. 11 shows an exemplary illustrative track 500 that includes a categorization station 502 and a sample processing station 504. It should be appreciated, that in most embodiments, a plurality of sample processing stations may be used, allowing samples to interact with multiple stations to perform various tests. In this illustrative embodiment, characterization station 502 is served by sidecar 506, which allows samples to enter the characterization station from the main track, rather than proceeding on track 508. Processing station 504 is serviced by sidecar 510. Characterization station 502 can characterize the geometry of each carrier and or the geometry of samples relative to positions in the carrier. Once a carrier is characterized, the carrier can proceed to processing station 504 where pipette 512 can access a sample transported by the carrier. For example, carrier 514 may be characterized by characterization station 502 to determine an offset in the normal stopping position for the carrier when the carrier 514 visits processing station 504. Once an offset is determined, carrier 514 can stop a predetermined distance from a stopping position, such as an optical mark, Hall effect sensor, or magnet, which will allow the center of a sample tube transported by carrier 514 to come to rest at a nominal stopping position for interaction with pipette 512.

FIG. 12 illustrates an exemplary way that a longitudinal offset may be used to position the center of a tube at a nominal position for interacting with a pipette, even where an offset includes a lateral component. In this illustrative embodiment, carrier 520 can be positioned for interaction with pipette 522 when moving along the track 524. In this example, pipette 522 is part of a radially moving pipettor. Pipette 522 moves in arc 526. In this example, pipette 522 can come to rest at any position along arc 526. Because arc 526 includes both longitudinal and lateral components relative to automation track 524, carrier 520 may be positioned such that the centerline 528 of a sample vessel intersects with arc 526, even when there is a lateral positioning error in the sample tube. By adjusting the position of the carrier 520 in direction 530, both lateral and longitudinal errors can be accounted for, allowing centerline 528 to intersect arc 526. For example, if a lateral positioning error exists where the centerline of the sample tube is toward the top of the page relative to a nominal stopping location, carrier 520 may be moved to the left, allowing centerline 528 to intersect arc 526 (e.g., intersect the arc a small amount counterclockwise from nominal). Similarly, if the centerline 528 is located right of nominal (i.e., toward the bottom of the page), carrier 520 can be moved forward (to the right of the page) along direction 530, allowing pipette 522 to move clockwise to intersect centerline 528 along arc 526.

It should be appreciated that linearly moving pipettors can also be used in some embodiments, and these can also allow either lateral or longitudinal offset correction. For example, a linear pipette may be placed to move transversal across the track, allowing access to vessels that are on the track or off the track. Once a lateral offset has been determined, the pipette may be moved to a lateral position coincident with the centerline 528. In some embodiments, the pipette of a linear or radial pipettor only allows a fixed location for aspirating on the track. In these embodiments the stopping position of the carrier can be adjusted by the track or the carrier to place the centerline of a sample vessel at a longitudinal position coincident with the aspiration point. In some embodiments carriers or the track may also be able to affect the lateral positioning of the stopping point of the carrier to allow the centerline to be aligned laterally with a the aspiration point.

FIG. 13 shows an exemplary embodiment whereby a mechanical device can be used to provide precise alignment of a carrier at an arbitrary longitudinal offset. Some embodiments use components that are integral to a track, such as magnets, rollers, or precision belts. Some embodiments can also use a wedge 532 to position centerline 528 of a sample carried by carrier 520 at an arbitrary position in the longitudinal direction to account for any longitudinal position errors in the placement of the sample tube. By moving wedge 532 in direction 534, moving the wedge in and out of the track 524 in the lateral direction, wedge 532 can create a hard stopping position at an arbitrary distance 536 from the front of the wedge. Wedge 532 can be moved in direction 534 using any suitable actuation means, such as a pneumatic, spring, or electromagnetic actuator. If carrier 520 moves in direction 538, carrier 520 can come to rest at a position that utilizes distance 536 to place the centerline 528 of a sample tube at an arbitrary longitudinal position to account for any offsets in tube placement, allowing centerline 528 to be placed at a nominal position for the line of action of a pipette or other instrument.

It should further be appreciated that these principles discussed with respect to pipettes can apply to other stations, such as aligning the centerline of a sample vessel with the line of action of robot arm in a sample-handling station or a decapper tool in a decapper or recapper station. Accordingly, although examples throughout may be commonly described with reference to the pipette of an instrument, such as a testing station, embodiments may be used to characterize an offset and align a sample tube for interacting with other tools in other stations, such as sample handling stations or decapper/recapper stations.

Figure 14:
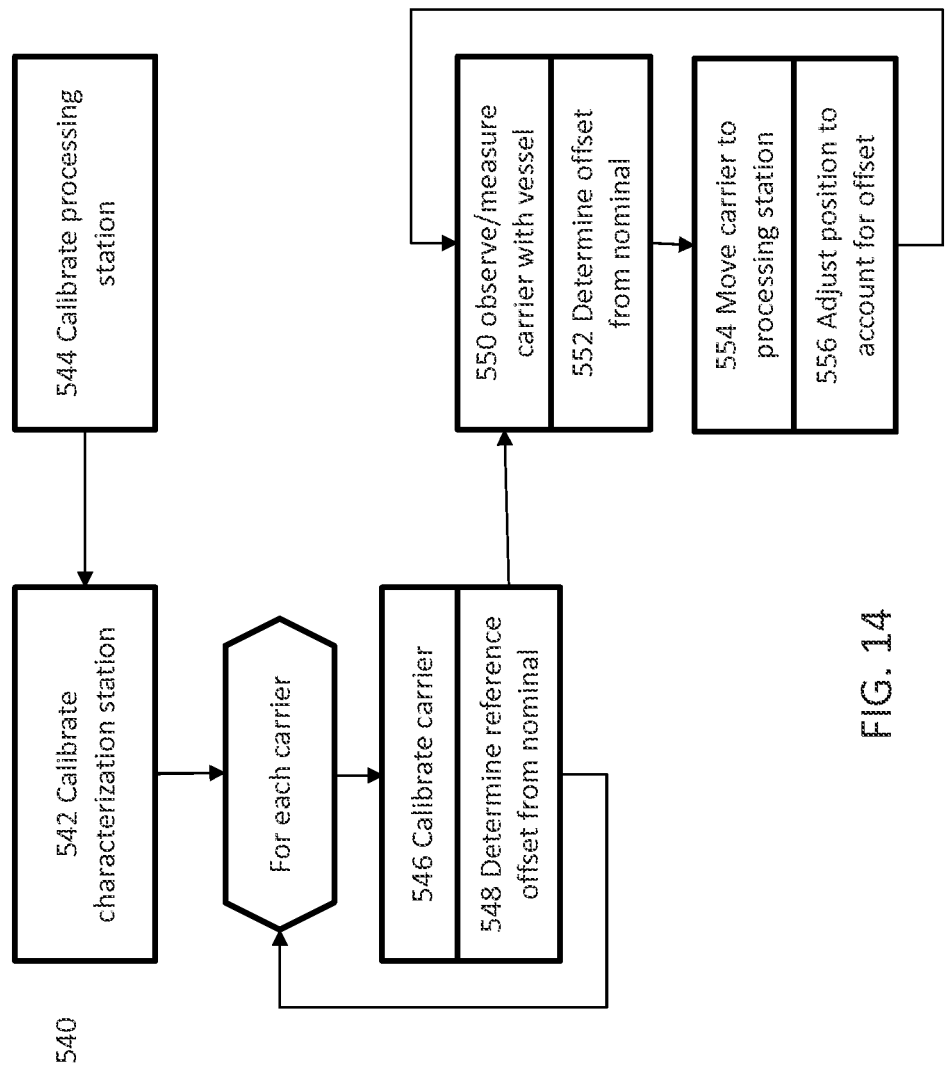
FIG. 14 is a flow chart of an exemplary characterization and positioning method for use with some embodiments.

FIG. 14 shows the exemplary process flow 540 for use with some embodiments. In some embodiments, the stations that interact with samples can be calibrated during a preliminary step. This can include using a maintenance carrier or reference device to determine if the alignments between the track and components of an instrument are at nominal positions or if an offset should be considered when interacting with these instruments. For example, a pipette in a sample processing station may be ideally aligned with position "0" on the local track section but, due to manufacturing tolerances, installation problems, wear, etc., the line of action for the pipette tip may be at a position 2 mm from nominal. This information can be considered when samples are handled by the pipette. For example, a carrier with nominal positioning may apply an offset of 2 mm to align the center of a sample with the line of action of the pipette.

Similarly, the calibration station itself may need to be calibrated. This can include an optical calibration whereby cameras are aligned with reference images to ensure that the calibration of each carrier corresponds with real-world offsets that should be applied to the carriers. For example, a tightly toleranced carrier can be provided as a reference carrier that can be calibrated to include known distances between a reference sample tube and a reference position on the carrier. A characterization station may attempt to characterize the reference carrier. Any errors found in the characterization of the reference carrier can be zeroed out by adjusting the interpretation of images by the calibration station. This can ensure that subsequent carriers that may be manufactured with lesser tolerances can be properly characterized by the characterization station.

In some embodiments, the calibration steps may utilize maintenance carriers, which may be manually or automatically deployed on an automation track. Suitable maintenance carriers and deployment mechanisms may include those disclosed in PCT Patent Application No. PCT/US13/64321, filed Oct. 10, 2013, and PCT Patent Application No. PCT/US13/64635, filed Oct. 11, 2013, each of which is incorporated by reference herein in its entirety.

At step 542, one or more characterization stations in an automation system can be calibrated to ensure accurate characterization of samples and carriers during runtime operation of the automation system. Similarly, at step 544 processing stations may be calibrated such that the line of action of any devices interacting with the automation track can be characterized and accounted for during runtime operation. In some embodiments, multiple characterization stations may be calibrated and used during runtime operations to provide further precision in characterizing samples relative to carrier positions.

In some embodiments, multiple calibration steps may occur for other components of the system, such as the automation track and any components that provide motive forces for carriers. In some embodiments, calibration steps 542 and 544 may be repeated at regular intervals, such as daily or the beginning of each shift. In some embodiments, calibration steps are only performed during initial installation of an analyzer automation system or on-demand.

Calibration steps 546 and 548 may be performed on each carrier that will use the automation system. These steps may be performed at regular intervals or upon request. Calibration step 546 may allow each carrier to be characterized while holding a reference sample. This may allow each carrier to provide a baseline for the expected position of carriers during runtime. This calibration step can be performed by characterizing each carrier and subsequently interacting with the carrier at processing stations to verify that a line of action of an instrument, such as a pipette, coincides with the center of a reference sample vessel. At step 548, a reference offset is determined from this calibration step. The reference offset is the baseline offset that will be assumed for samples carried by the carrier at runtime. It should be appreciated that the reference offset may refer to a single edge of a tube or the center point of a tube, which may vary depending on tube size. Accordingly, a plurality of reference offsets may be calculated for each carrier for various standard tube-sizes that can be transported.

Determination step 548 may be carried out automatically using a processor that interacts with the automation system. This processor may be used during runtime to determine offsets and to direct carriers to specific stopping locations for interaction with instruments. This processor may also receive information from calibration steps 542 and 544. In some embodiments, the processor participates in the calibration steps 542 through 546.

In some embodiments, steps 546 and 542 are optional. In some embodiments, each time a tube is placed in a carrier the tube and carrier combination is characterized. In some embodiments, this characterization may utilize the reference offset from step 548 to compare the tube placement to the nominal tube placement determined at step 548. In other embodiments, reference offsets for each carrier are not used and each carrier vessel combination is characterized without any prior knowledge of the expected location of the vessel being carried.

At step 550, after a carrier receives a vessel, such as a sample tube, the carrier and vessel combination is characterized by at least one characterization station. This characterization station may be placed in any suitable position along the automation system, such as at a sample handling station where the tube is first placed into the carrier. In some embodiments, characterization step 550 can occur multiple times at multiple calibration stations. In some embodiments, calibration stations may be provided for each module within the automation system, allowing each module to make an independent determination of the proper offset to use when handling the carrier and vessel on local automation tracks. In some embodiments, step 550 occurs immediately before the carrier is placed in position to interact with an instrument, such as a pipette. This may allow the most up-to-date offset to be used.

Measurement 550 can include optically observing the carrier and sample vessel. Observation can include optical measurement of distances and relative locations of components of a carrier and the vessel being transported. This can include using an electro-optical device, such as a camera, a laser and photo detector, IR rangefinders, projectors, lenses, etc. In some embodiments, measurement 550 can include mechanical measurements, such as feelers that determine where a carrier has stopped and where a vessel being transported has stopped in a characterization station. In some embodiments, magnetic devices, such as Hall effect sensors may be used to determine a precise location of a surface of a carrier to provide a reference position when measuring the location of a sample vessel carried by the carrier.

The observation in step 550 can include determining one or more distances between points in the carrier, such as a reference point on the carrier and the leading and trailing edge of the sample vessel. This can be used to provide a reference location of the edge or center of the vessel relative to the reference point on the carrier. By subsequently positioning the carrier and the reference point, the edge or center of the vessel can also be precisely placed. In some embodiments, measurement 550 includes detected location of an edge or center of the sample vessel in an image. This location can then be compared to the expected location of the vessel.

The observations from step 552 can be communicated to a processor. This may include local signaling with a local processor or communicating across a network to a processor for calculation of an offset to account for the observed positioning of the sample vessel.

Once the carrier and vessel combination has been measured, at step 552, a processor can determine an offset from a nominal position, or any reference point in the carrier. For example, where a carrier has been calibrated at steps 546 and 548, the carrier may include a nominal position, which is the expected position of the centerline of a sample tube being carried. The measurement received from step 550 may show a difference between the detected centerline of a sample vessel and the nominal centerline of the sample vessel. This can be added to any offset determined by step 548. In some embodiments, an offset is calculated by determining the centerline of a sample tube from step 550 relative to a reference point on the carrier. The offset may be the distance between centerline of the sample tube and the reference point on the carrier. Subsequently, when the carrier is placed for interaction with a pipette, the reference point on the carrier can be placed at a distance equal to the offset from the centerline of the center of the tube, so that the center of the sample tube and the line of action of the pipette are roughly coincident. Steps 550 and 552 can occur automatically for each sample placed on an automation system.

At step 554, the carrier is moved from the characterization station to a position to interact with one or more processing stations within the automation system. For example, this can include a station that aspirates a portion of a sample contained in a sample vessel for use in any number of suitable tests. Once a carrier is moved to the processor station, the carrier can be precisely positioned such that the center of the vessel it transports is coincident with the line of action of any instrument, such as pipettes. This can be accomplished by adjusting the reference position of the carrier by the offset calculated at step 552. Step 556 may be carried out at the direction of the processor that calculates the offset at step 552 or may be carried out by another processor that operates responsive to the offset received from a processor calculating the offset at step 552. The adjustment at step 556 can also take any calibration information derived from step 544 into account. For example, the calibration of processing station may identify the nominal position for a sample when interacting with pipette. This may be considered when calculating the final position of the carrier to align the line of action of the pipette with the centerline of the vessel being carried.

Figure 15:
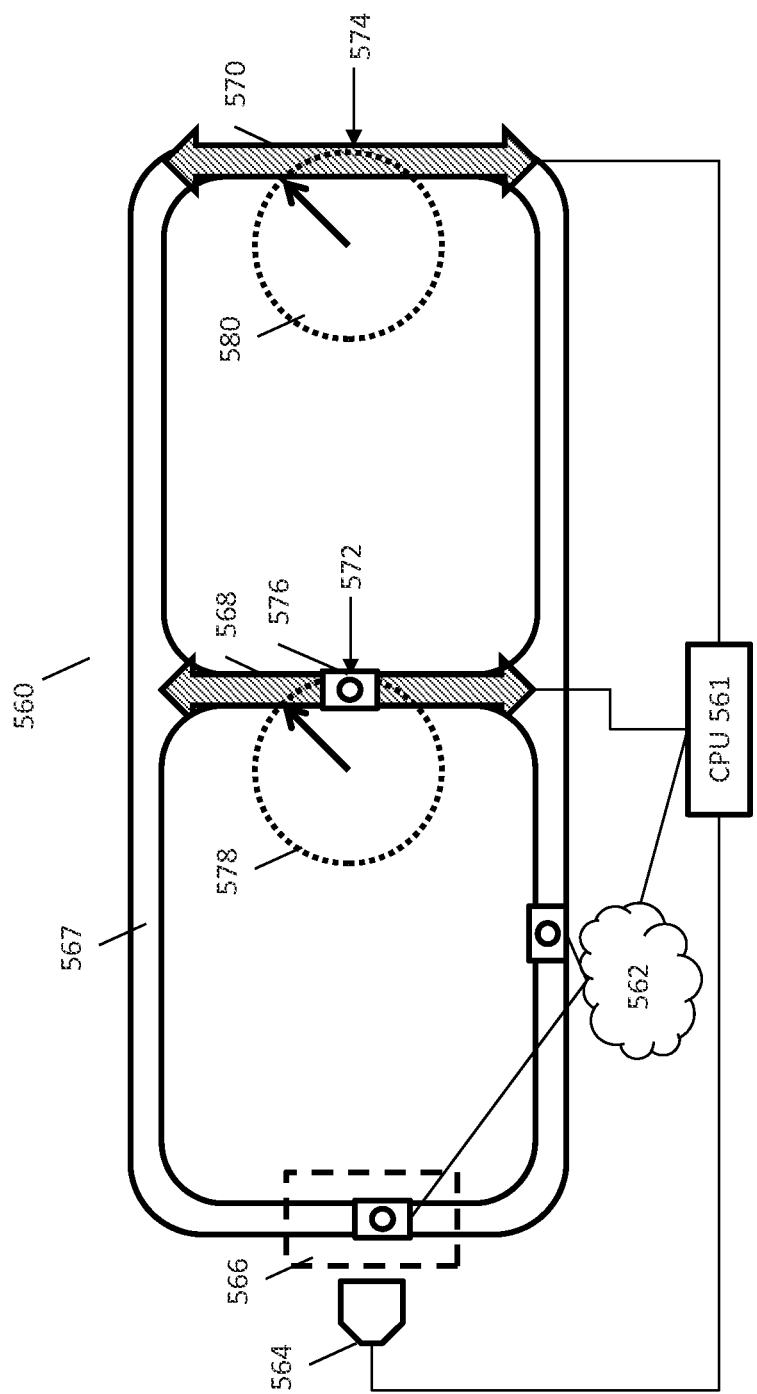
FIG. 15 is a top view of an exemplary automation system for use with some embodiments.

FIG. 15 depicts the system architecture for an exemplary system for use with some embodiments. Automation system 560 includes a processor 561 that directs the activities of the automation system. Processor 561 can interact with components of automation system 560 via network 562 or through direct connections. Network 562 can include a wireless or Ethernet-based network. Processor 561 can interact with optical measuring device 564, which operates at characterization station 566 to characterize carriers. In some embodiments, processor 561 can also communicate directly with carriers, such as carrier 576. This can allow processor 561 to issue routing instructions where carriers are configured to operate semi-autonomously and route through the automation system.

Carriers can traverse automation system 560 using track 567. Once a carrier is characterized by characterization station 566, the measurements taken by optical measuring device 564 can be communicated to processor 561. Processor 561 can then calculate an offset to apply to each carrier at each station 578 and 580 in the automation system. In some embodiments, processor 561 can also communicate with and control local track positioning devices, such as local tracks 568 and 570. These can include friction or magnetic tracks that can be operated with fine precision to precisely position carriers, such as carrier 576, at positions on the local automation track. For example, carrier 576 may be positioned at an offset from reference position 572 on track 568. Reference position 572 may be a nominal position for station 578 (or a position that should coincide with a reference position on a carrier under nominal conditions). Carrier 576 may be positioned such that a reference position within carrier 576 is placed at an offset from position 572 in accordance with the offset determined by processor 561, such that the center of a sample vessel being carried by carrier 576 aligns with the line of action of a pipette at station 578. Similarly, station 580 may have a reference position 574 which may be used for applying an offset to carriers interacting with pipettes in station 580.

In typical prior art systems, the motion of local pipettor arms and robot arms is controlled by a local processor. In some embodiments, processor 561 can also communicate with local processors that control the instruments at stations 578 and 580. For example, where station 578 includes a local processor that directs the motion of a radially moving pipettor arm, the motion of that pipettor arm can be used to correct an offset observed by the characterization station. An example of this motion is discussed with respect to FIG. 12. Once processor 561 determines a lateral or longitudinal offset, processor 561 can communicate via convention protocols, such as IP or CAN, to local processors to coordinate the motion of local interaction devices, such as pipettor arms or robot arms to account for the observed offset. In some embodiments, once processor 561 determines the offset for each sample vessel, the carrier can be moved to a fixed stopping location and the offset can be conveyed to the local processor to move local interaction devices appropriately to counteract the offset. In this manner, processor 561 can act as a central positioning error correction processor that facilitates the compensation for lateral and/or longitudinal offsets. A central positioning error correction processor the system may communicate with both the track and the individual instruments/robotic devices in order to coordinate the positioning of the sample vessel and the pipettor/robotic end effectors.

FIG. 16 shows an exemplary embodiment of an optical measuring device. While some embodiments utilize cameras to perform pixel-based measurement of distances, photo detector-based measuring devices can also be used in some embodiments. In the embodiment shown in FIG. 16, a plurality of LEDs is used to detect objects that pass by. One or more photo detectors placed on the opposite side of the track from LEDs A and B can detect an object passing through the beams created by the LEDs. Carrier 582 holds sample tube 581, which has a centerline 585. Centerline 585 indicates the nominal line of action for interacting with sample tube 581. Signals 586 and 587 depict the information that may be provided by photo detectors detecting light emitted from LEDs A and B. Dark sections in signals 586 and 587 can indicate that the object has tripped the beams from LEDs A and B, indicating that an object has passed through.

It should be appreciated, that embodiments that utilize LED/photo detector combinations may allow rapid timing-based measurements of object sizes and distances. For example, if a carrier has a known size, the size of the shadow cast as the carrier passes through a light beam can translate to the timing in the resulting signal where no light is detected. For a carrier moving at an arbitrary speed, this information can be used to map time to distance. Accordingly, when a shadow of a sample tube is detected, the resulting signal can be mapped to precise distances relative to the edges of the carrier.

Signal section 588 indicates that sample tube 581 has tripped beam A. This may effectively reveal the shadow of sample tube 581. In some embodiments, where tube 581 is glass or transparent plastic, signal section 588 may not indicate the absence of light, but the resulting refraction and scattering may indicate a change in the light detected from LED A. Signal section 589 indicates the shadow of carrier 582 as it passes between LED B and a photo detector. Signal sections 589 and 588 can be compared in the time domain to determine certain distances, which may be used to determine the location of centerline 585 relative to the edges of carrier 582. For example, the difference between the leading edge of sample tube 581 and carrier 582 can be calculated to be distance 590. By examining the overall length of signal 589, the amount of time in distance 590 can be translated to a real-world distance that indicates the real world distance between the leading edge of the sample tube and the leading edge of the carrier. Distance 592 can indicate the width of sample tube 581. A processor examining signals 586 and 587 can determine that centerline 585 is at the center of distance 592. Accordingly, a processor examining the signals can determine a precise distance offset from the leading edge or trailing edge of a carrier that coincides with the centerline of a sample tube being carried.

Figure 17:
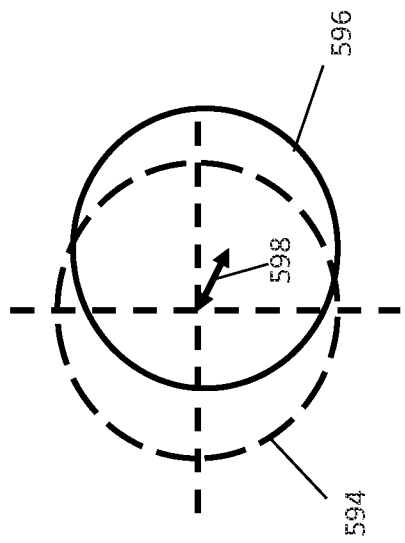
FIG. 17 is a top view of an exemplary characterization scenario for use with some embodiments.

FIG. 17 shows an example of how a camera may be used to provide precise offset information. A reticle 594 may be provided in the lens of a camera or may be provided digitally by mapping certain pixels (i.e., a pixel mapping) in an image plane to reference points that are predetermined as indicating the nominal position for a sample tube. In this embodiment, reticle 594 may be provided for a downward facing camera, which observes the top of tubes passing underneath the camera. Tube 596 may pass through the image and be observed at an offset 598 from the nominal positioning. For example, a carrier can come to rest at a nominal position in a characterization station. For an ideal sample tube, the image of the tube and reticle 594 should align. An offset in the image indicates an offset in the physical placement of the top of the sample tube in the real world. Accordingly, the processor can compare the image of tube 596 to an optical reticle 594 or a virtual reticle that is indicated by the expected pixel locations for the edges of tube 596.

In some embodiments, a variably sized reticle may be used, such that a camera can determine the size of a tube and select a properly sized and shaped virtual reticle to compare to an image of the tube. In some embodiments, a single reticle can be used and the processor can compare the reticle to an image of the tube and determine the concentricity of the tube in the reticle to determine an offset for the center of the tube.

Figure 18:
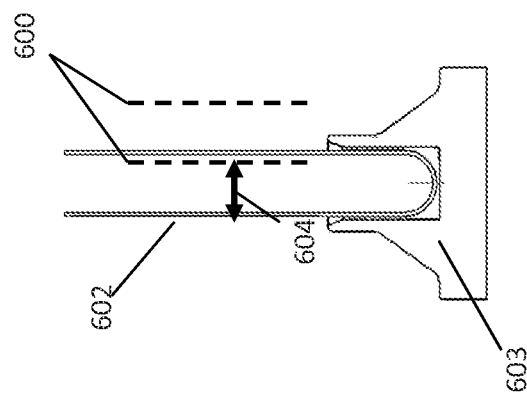
FIG. 18 is a side view of an exemplary characterization scenario for use with some embodiments.

FIG. 18 shows an exemplary use of a camera using reticles to determine offsets, where the camera is a side facing camera. Reticle 600 can be compared to tube 602, which may be transported by carrier 603. A side facing camera may take an image of tube 602 as carrier 603 passes through or comes to rest at a nominal position. By examining the location of the sidewalls of sample tube 602 in the image plane, reticle 600 can be compared to determine a distance 604. Reticle 600 may be etched into optics used by the camera or may be a virtual reticle that maps the expected location of sidewalls of tube 602 to pixel locations in an image.

Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

What is claimed is:

1. A method for aligning a sample vessel relative to instruments in an automation system in an in-vitro diagnostic (IVD) environment comprising steps of:
measuring at least one distance between a reference point in a carrier and a position of a vessel within the carrier;
automatically determining, using a processor, an offset between the vessel position and a nominal position based on the at least one distance;
moving the carrier to a station within the automation system for interaction between a sample contained in the vessel and the station; and
positioning the carrier at a location accessible to the station, the location being chosen to compensate for the offset.

2. The method of claim 1, further comprising aspirating a portion of the sample using a pipette once the carrier has been positioned at the location.

3. The method of claim 1, wherein the step of measuring the at least one distance comprises observing the carrier and vessel with at least one camera.

4. The method of claim 1, wherein the step of measuring the at least one distance comprises observing the carrier and the vessel using an LED and an electro-optical device.

5. The method of claim 1, wherein the steps of measuring and automatically determining an offset are repeated when another vessel is inserted into the carrier.

6. The method of claim 1, further comprising calibrating a line of action of the station.

7. The method of claim 1, wherein a measuring station performs the measuring step and the measuring station is calibrated using a reference carrier prior to performing the measuring step.

8. The method of claim 1, wherein a measuring station performs the measuring step and the measuring station, calibrates the carrier prior to performing the measuring step.

9. A method for aligning a sample vessel relative to instruments in an automation system in an in-vitro diagnostic (IVD) environment comprising steps of:
observing a sample vessel carried by a carrier to compare an observed position of the sample vessel to a predetermined nominal position;
automatically determining, using a processor, an offset that accounts for the comparison of the observed position and the predetermined nominal position of the vessel;
moving the carrier along an automation track to a processing station for interaction between a sample contained in the vessel and the station; and
positioning the carrier at a location accessible to the station utilizing the offset such that the sample is placed at a predetermined location relative to the station.

10. The method of claim 9, further comprising aspirating a portion of the sample using a pipette once the carrier has been positioned at the location.

11. The method of claim 9, wherein the step of observing comprises observing the carrier and vessel with at least one camera.

12. The method of claim 9, wherein the step of observing comprises comparing an image of the sample to a pixel mapping of the predetermined nominal position of the vessel in the image.

13. The method of claim 9, wherein the steps of observing and automatically determining an offset are repeated when another vessel is inserted into the carrier.

14. The method of claim 9, wherein the step of observing is performed by a characterization station located on the automation track.

15. The method of claim 9, wherein the step of positioning the carrier comprises positioning the carrier such that the centerline of the vessel is substantially coincident with an arc of movement of a pipette controlled by the station.

16. An automation system for use with a clinical chemistry analyzer comprising:
at least one processor;
an automation track configured to facilitate moving a plurality of carriers holding samples between a plurality of stations; and
a characterization station configured to observe sample vessels in a plurality of carriers on the automation track and communicate observation information to the at least one processor,
wherein the at least one processor is configured to determine an offset corresponding to a distance between the centerline of each sample and a nominal position of each corresponding carrier from the information received from the characterization station and facilitate positioning of each corresponding carrier at a stopping position on the automation track, the specific location of the stopping position being determined by the offset such that the centerline of each sample aligns with a predetermined position accessible to one of the plurality of stations in an analyzer.

17. The automation system of claim 16, wherein each carrier is configured to hold each sample vessel substantially vertically by applying a spring force to hold each sample vessel against at least one vertical tine.

18. The automation system of claim 17, wherein each carrier is further configured to utilize a plurality of vertical tines to hold each sample vessel in substantially a transverse center of at least two tines.

19. The automation system of claim 16, wherein the at least one processor is further configured to facilitate stopping each carrier at the stopping position such that the centerline of the vessel is substantially coincident with an arc of movement of a pipette controlled by one of the plurality of the stations.

20. The automation system of claim 16, wherein the characterization station comprises at least one electro-optical device configured to capture an image of each vessel.

21. The automation system of claim 16, wherein the characterization station comprises at least one electro-optical device configured to detect when a sample vessel passes the electro-optical device.

22. The automation system of claim 16, wherein each of the plurality of stations comprises an instrument having a pipette.

23. The automation system of claim 16, wherein at least one of the plurality of stations comprises a sample processing station.

24. A method for aligning a sample vessel in an automation system in an in-vitro diagnostic (IVD) environment comprising steps of:
observing a sample vessel carried by a carrier to compare an observed position of the sample vessel to a predetermined nominal position;
automatically determining, using a first processor, an offset that accounts for the comparison of the observed position and the predetermined nominal position of the vessel;

moving the carrier along an automation track to a processing station for interaction between a sample contained in the vessel and the station;

stopping the carrier at a predetermined location at the processing station; and positioning an interaction device of the station at a location relative to the carrier that varies according to the offset determined for the carrier, such that interaction device aligns with the sample vessel.

25. The method of claim 24, wherein the interaction device is a pipette and the method further comprises aspirating a portion of the sample using the pipette once the carrier has stopped.

26. The method of claim 24, wherein the step of observing comprises observing the carrier and vessel with at least one camera.

27. The method of claim 24, wherein the step of observing comprises comparing an image of the sample to a pixel mapping of the expected location of the vessel in the image.

28. The method of claim 24, wherein the steps of observing and automatically determining an offset are repeated when another vessel is inserted into the carrier.

29. The method of claim 24, wherein the step of observing is performed by a characterization station located on the automation track.

30. The method of claim 24, wherein the step of stopping the carrier comprises positioning the carrier such that the centerline of the vessel is substantially coincident with an arc of movement of the interaction device, wherein the interaction device is a pipette.

31. The method of claim 24, wherein the interaction device is a pipette.

32. The method of claim 24, wherein the interaction device is a robot arm.

33. The method of claim 24, wherein the step of positioning the interaction device occurs responsive to the control of a second processor in communication with the first processor.

34. The method of claim 24, wherein the offset includes a lateral component relative to the automation track, and the step of positioning the interaction device includes laterally positioning the interaction device.

* * * * *